US012569451B2

(12) United States Patent
Cho et al.

(10) Patent No.: US 12,569,451 B2
(45) Date of Patent: Mar. 10, 2026

(54) BIO-INSPIRED TISSUE-ADHESIVE HYDROGEL PATCH AND USES THEREOF

(71) Applicant: CELLARTGEN INC., Seoul (KR)

(72) Inventors: Seung Woo Cho, Seoul (KR); Ji Soo Shin, Seoul (KR); Soo Jeong Choi, Seoul (KR); Dong Hoon Choi, Seoul (KR)

(73) Assignee: CELLARTGEN INC., Seoul (KR)

( * ) Notice: Subject to any disclaimer, the term of this patent is extended or adjusted under 35 U.S.C. 154(b) by 756 days.

(21) Appl. No.: 17/597,464

(22) PCT Filed: Oct. 17, 2019

(86) PCT No.: PCT/KR2019/013673
§ 371 (c)(1),
(2) Date: Jan. 6, 2022

(87) PCT Pub. No.: WO2021/006426
PCT Pub. Date: Jan. 14, 2021

(65) Prior Publication Data
US 2022/0280442 A1 Sep. 8, 2022

(30) Foreign Application Priority Data

Jul. 9, 2019 (KR) ........................ 10-2019-0082681
Jul. 9, 2019 (KR) ........................ 10-2019-0082682

(51) Int. Cl.

| | |
|---|---|
| A61K 9/70 | (2006.01) |
| A61K 9/06 | (2006.01) |
| A61K 35/28 | (2015.01) |
| A61K 38/18 | (2006.01) |
| A61K 47/10 | (2017.01) |
| A61K 47/36 | (2006.01) |
| A61P 17/02 | (2006.01) |
| C12N 5/0775 | (2010.01) |

(52) U.S. Cl.
CPC .............. *A61K 9/7023* (2013.01); *A61K 9/06* (2013.01); *A61K 35/28* (2013.01); *A61K 38/1858* (2013.01); *A61K 38/1866* (2013.01); *A61K 47/10* (2013.01); *A61K 47/36* (2013.01); *A61P 17/02* (2018.01); *C12N 5/0667* (2013.01); *C12N 2533/30* (2013.01)

(58) Field of Classification Search
CPC .. A61K 9/7023; A61K 35/28; A61K 38/1858; A61K 38/1866; A61K 47/10; A61K 47/36; A61P 17/02; C12N 5/0667; C12N 2533/30; A61L 27/52
See application file for complete search history.

(56) References Cited

U.S. PATENT DOCUMENTS

| | | | |
|---|---|---|---|
| 9,320,826 B2 | 4/2016 | Lee et al. | |
| 2005/0143484 A1* | 6/2005 | Fang .................... | A61L 24/0031 |
| | | | 523/122 |
| 2015/0306230 A1 | 10/2015 | Combs et al. | |
| 2020/0230288 A1* | 7/2020 | Cho .......................... | C08J 3/24 |

FOREIGN PATENT DOCUMENTS

| | | |
|---|---|---|
| JP | 2014514942 A | 6/2014 |
| JP | 2019509387 A | 4/2019 |
| KR | 1020160029941 A | 3/2016 |
| KR | 1020180038573 A | 4/2018 |
| KR | 1020180127634 A | 11/2018 |
| KR | 101942220 B1 | 1/2019 |
| KR | 1020190052547 A | 5/2019 |
| WO | 2012136701 A1 | 10/2012 |
| WO | 2013180458 A1 | 12/2013 |
| WO | 2018143736 A1 | 8/2018 |

OTHER PUBLICATIONS

Changhyun Lee, Jisoo Shin, Jung Seung Lee, Eunkyoung Byun, Ji Hyun Ryu, Soong Ho Um, Dong-Ik Kim, Haeshin Lee and Seung-Woo Cho, "Bioinspired, Calcium-Free Alginate Hydrogels with Tunable Physicaland Mechanical Properties and Improved Biocompatibility", Biomacromolecules 2013, 14, 2004-2013 (Year: 2013).*
Seonki Hong et al., "Hyaluronic Acid Catechol: A Biopolymer Exhibiting a pH-Dependent Adhesive or Cohesive Property for Human Neural Stem Cell Engineering", Advanced Functional Materials, 2013, 23, 1774-1780 (Year: 2013).*
European Search Report issued in European Application No. 19937259. 0, dated Jun. 15, 2023.
Xu Jinke et al. Genipin crosslinked catechol chitosan mucoadhesive hydrogels for buccal drug deliverty, biomateria ls, vol. 37, Jan. 1, 2015 , pp. 395 404.
Marie Krogsgaard et al. Mussel Inspired Materials Self Healing through Coordination Chemistry, Chemistry a European Jourmal, JHON Wiley&Sons, Inc, DE, vol. 22, No. 3, Nov. 12, 2015 , pp. 844 857.
International Search Report (with English translation) and Written Opinion of PCT/KR2019/013673 dated Apr. 8, 2020.

(Continued)

*Primary Examiner* — Sue X Liu
*Assistant Examiner* — Nathan W Schlientz
(74) *Attorney, Agent, or Firm* — HSML P.C.

(57) ABSTRACT

The present disclosure relates to a catechol group- or pyrogallol group-functionalized biocompatible polymer hydrogel patch having excellent biocompatibility and tissue adhesion, and uses for drug delivery, cell transplantation and tissue regeneration using the same. The biocompatible polymer hydrogel patch functionalized with the catechol group or pyrogallol group of the present disclosure has remarkably excellent mechanical properties and tissue adhesion compared with a solution-based bulk hydrogel. Therefore, it can load cells and a drug in vivo for a long time and also safely and efficiently deliver the cells and the drug to a target site.

11 Claims, 37 Drawing Sheets

(56)     References Cited

OTHER PUBLICATIONS

Jung Ho Cho et al., "Ascidian-Inspired Fast-Forming Hydrogel System for Versatile Biomedical Applications: Pyrogallol Chemistry for Dual Modes of Crosslinking Mechanism", Advanced Functional Materials, published Dec. 15, 2017, 10 pages provided.

Jui-Yang Lai, "Influence of Pre-Freezing Temperature on the Corneal Endothelial Cytocompatibility and Cell Delivery Performance of Porous Hyaluronic Acid Hydrogel Carriers", International Journal of Molecular Sciences, published Aug. 2015, 16 pages provided.

Shin et al., "Tissue Adhesive Catechol-Modified Hyaluronic Acid Hydrogel for Effective, Minimally Invasive Cell Therapy", Advanced Functional Materials vol. 25, Issue 25 pp. 3814-3824, First published May 15, 2015.

* cited by examiner

*FIG. 6B*
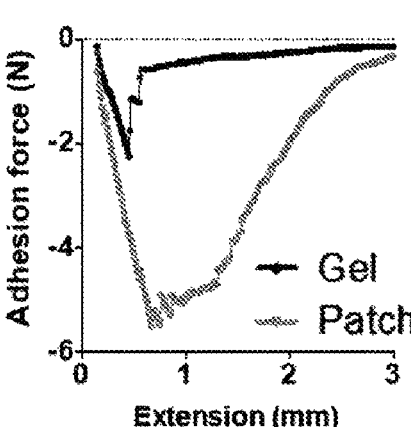
*FIG. 6C*
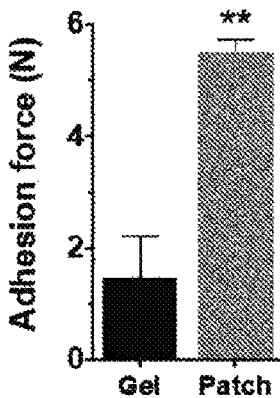 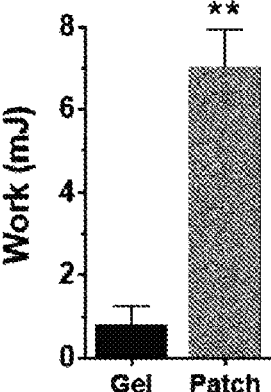

*FIG. 11A*  *FIG. 11B*
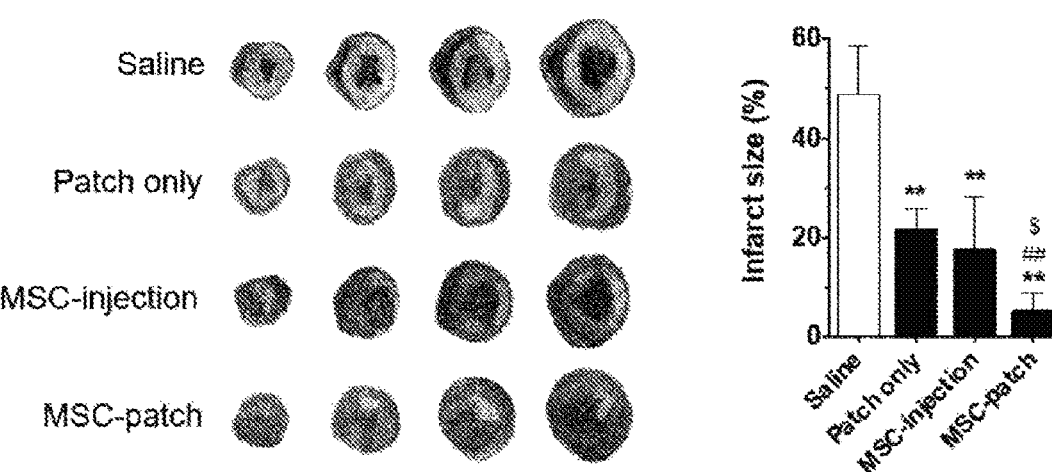
*FIG. 11C*  *FIG. 11D*
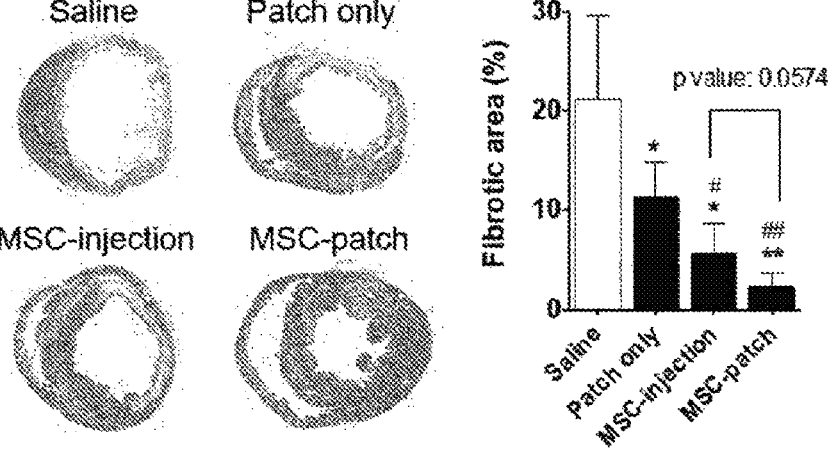

*FIG. 14A*
*FIG. 14B*
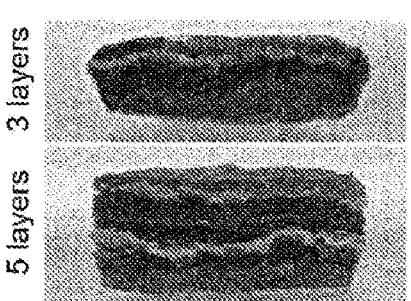
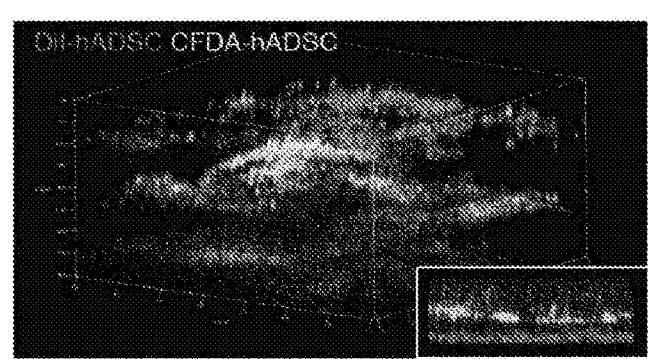
*FIG. 15A*
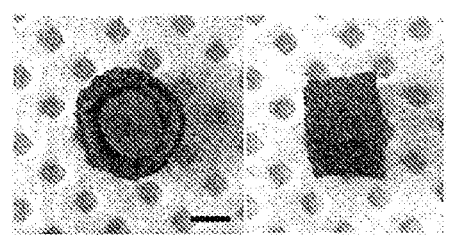
*FIG. 15B*
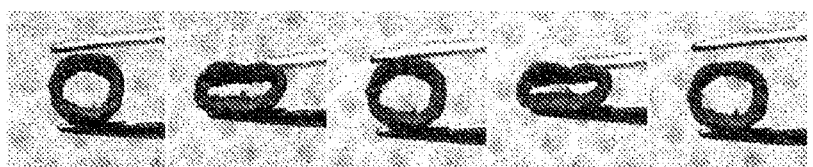

*FIG. 18A*                    *FIG. 18B*
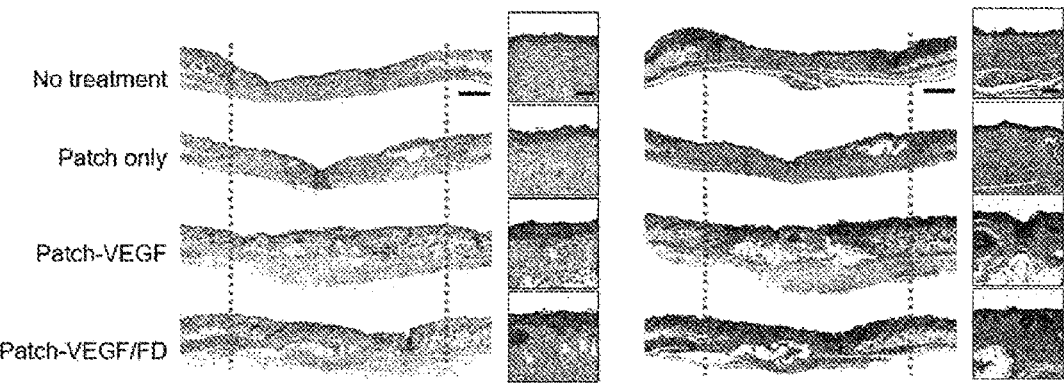
*FIG. 18C*        *FIG. 18D*
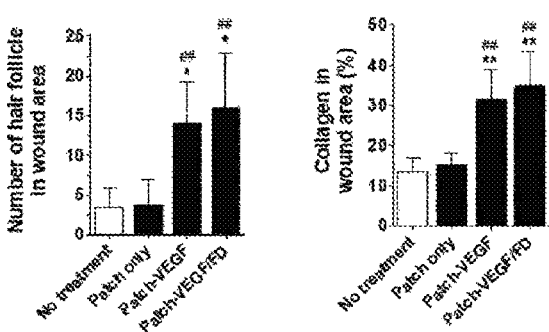
*FIG. 18E*
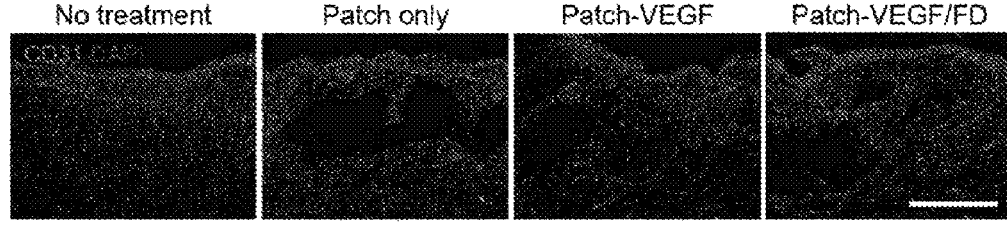

*FIG. 18F*
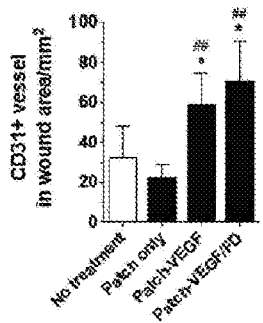
*FIG. 19B*
*FIG. 19A*
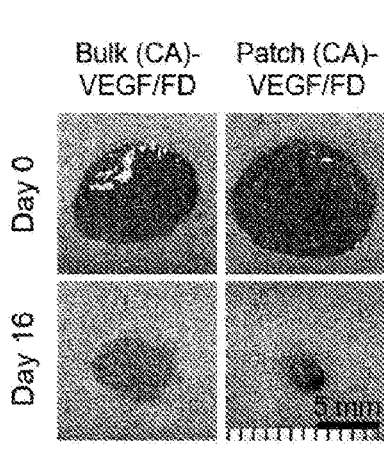
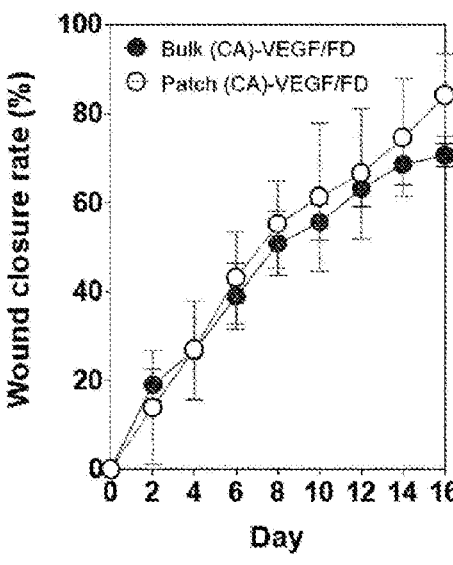

Bulk (CA)-VEGF/FD

Patch (CA)-VEGF/FD

Bulk (CA)-VEGF/FD

Patch (CA)-VEGF/FD

HA-pyrogallol (HA-PG)

*FIG. 22*
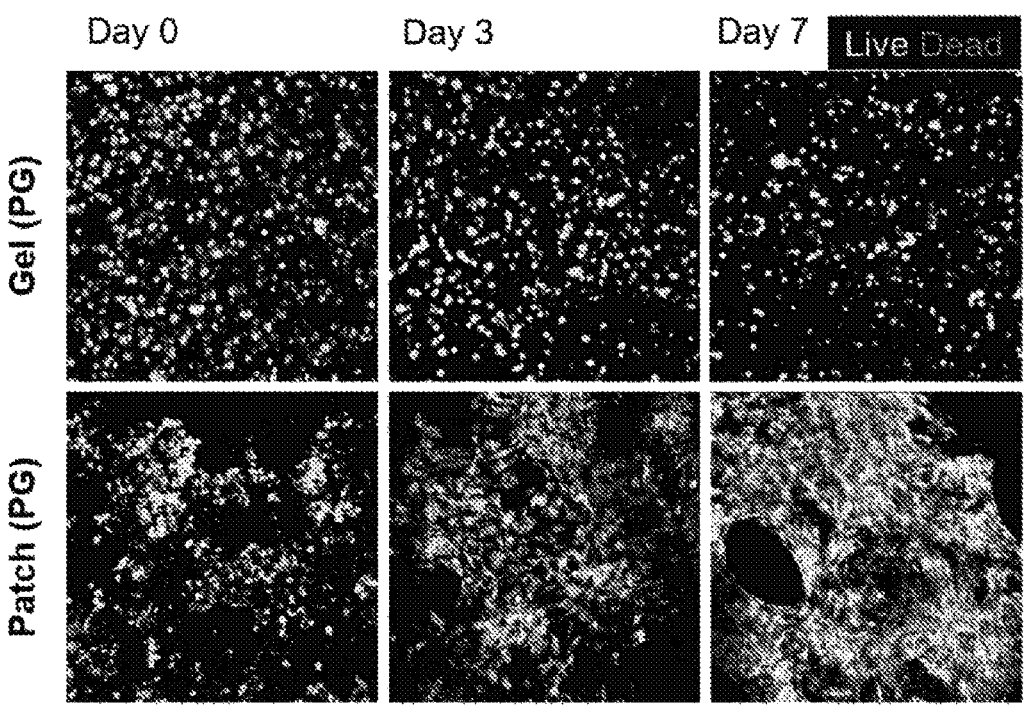
*FIG. 23B*
*FIG. 23A*
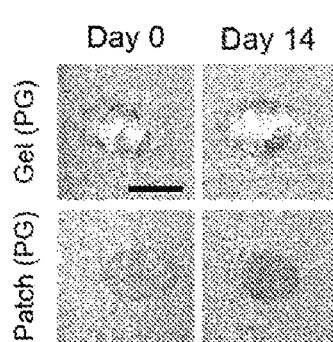
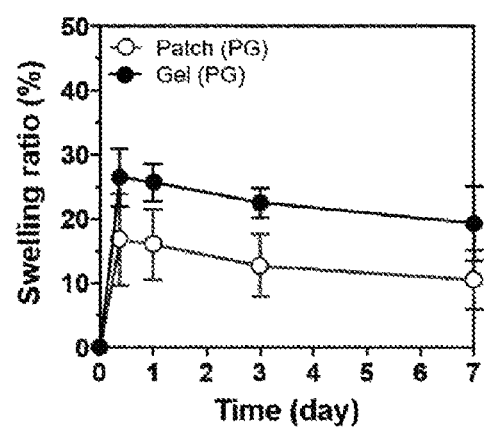

*FIG. 23C*
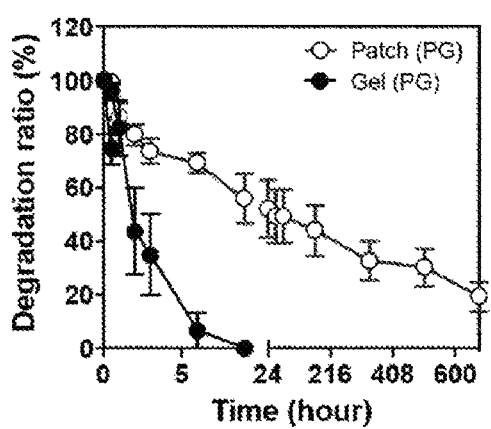
*FIG. 24*
Gel (PG)                                    Patch (PG)
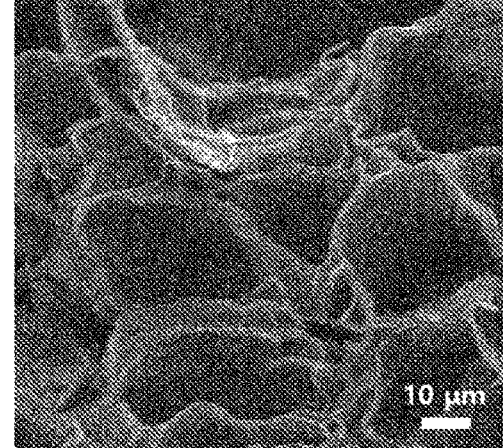          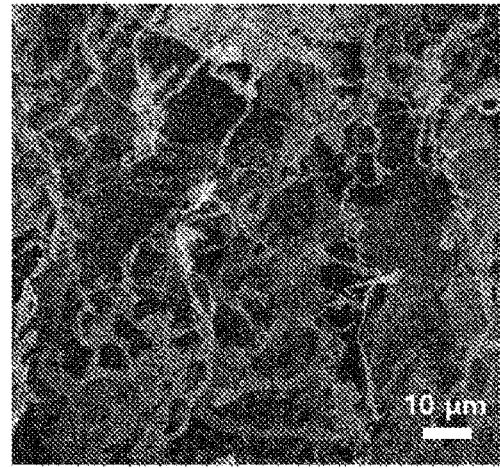

*FIG. 25A*
*FIG. 25B*
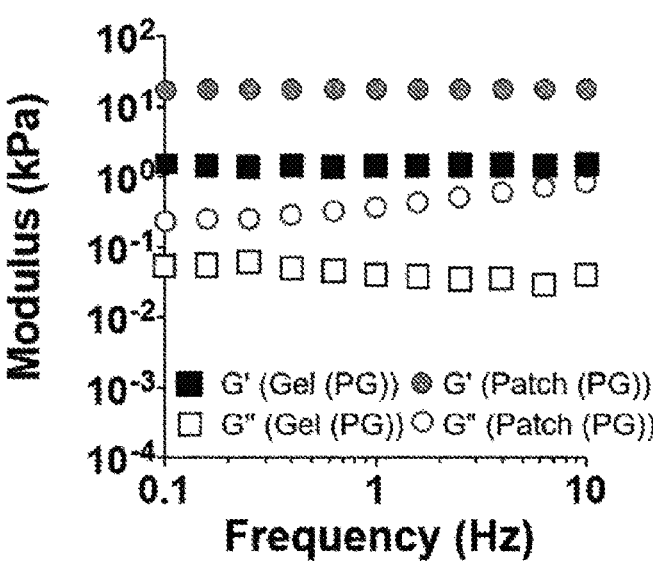
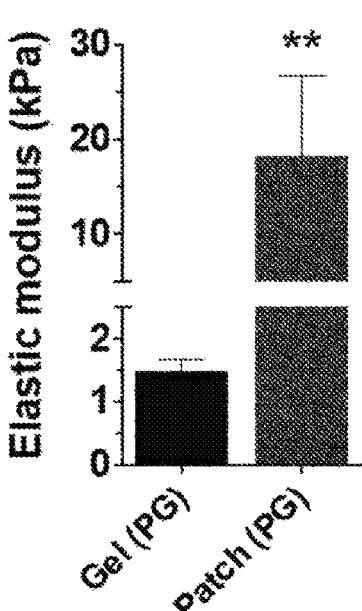
*FIG. 25C*
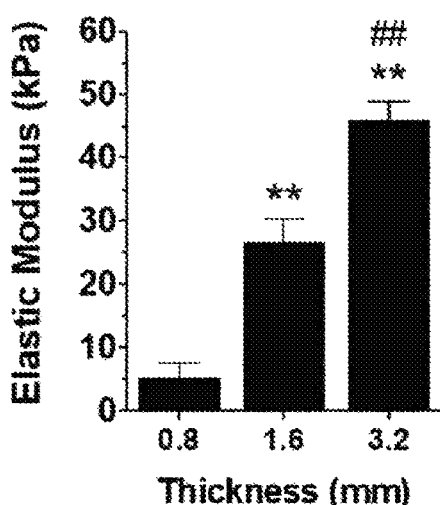

*FIG. 26A*
*FIG. 26B*
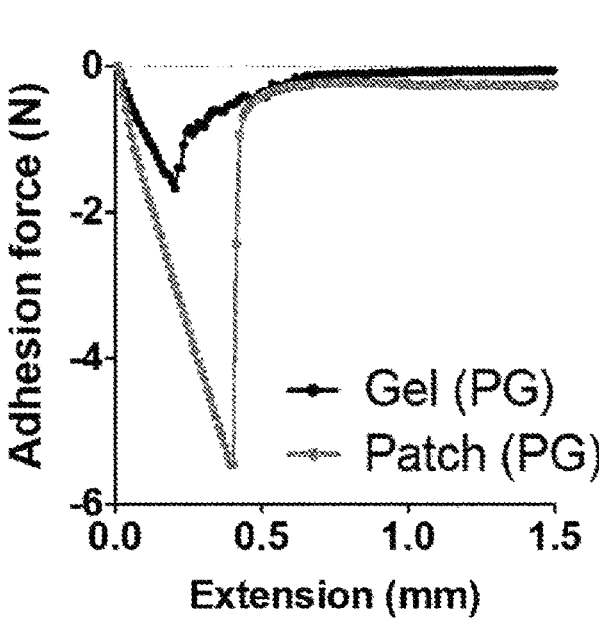
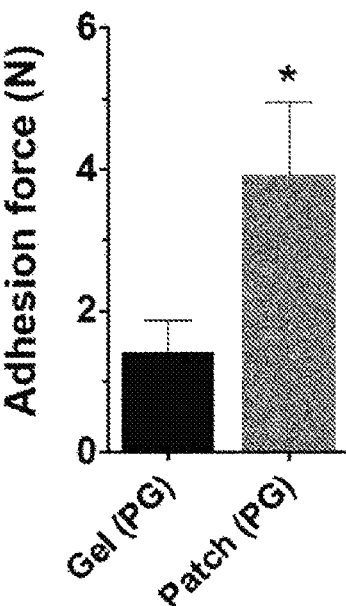
*FIG. 26C*
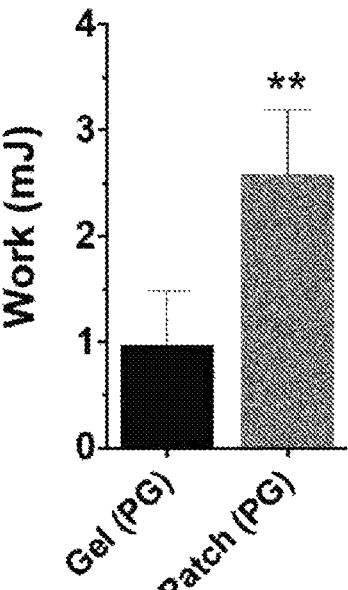

BIO-INSPIRED TISSUE-ADHESIVE HYDROGEL PATCH AND USES THEREOF

TECHNICAL FIELD

The present disclosure relates to a catechol group- or pyrogallol group-functionalized biocompatible polymer hydrogel patch having excellent biocompatibility and tissue adhesion, and uses for drug delivery, cell transplantation and tissue regeneration using the same.

BACKGROUND

In order to effectively recover tissues and organs damaged by diseases or accidents, a drug and cells need to be efficiently delivered in vitro and in vivo. Accordingly, many studies have been conducted to deliver a drug and cells, but systems that are used in clinical practice and exhibit satisfactory healing effects are still poorly developed.

In the case of cell delivery, conventionally, a direct injection method has been mainly used. However, this method may destroy cells by the pressure during injection, and may have risks of tissue damage and bleeding. To overcome this limitation, polymer patch-based cell delivery techniques have been developed, but sutures or glues still need to be additionally used to attach the patch onto the tissue surface. Also, suturing may cause direct damage to the tissue, and when a glue is used, a complete contact between the tissue and the patch loaded with the cells cannot be made so that the efficiency of cell delivery to the damaged tissue can be greatly reduced. The treatment time may also be prolonged due to additional treatment, and, thus, the healing effects can often be reduced.

In the case of drug delivery, conventional simple administration methods such as oral administration have a problem of short drug residence time due to rapid degradation and diffusion of drug, and the amount of drug to be injected or the frequency of drug injection has increased for effective treatment.

In order to solve the problems with the conventional drug and cell delivery methods, studies on delivery methods using hydrogels have been conducted. However, most of them relate to methods of loading and crosslinking a drug or cells in a hydrogel solution to induce gel formation. However, since the above method is applied in the form of injecting a hydrogel into a living body, the result is likely to vary depending on the user's skill level in handling the hydrogel and the user's convenience is greatly reduced. Further, since the hydrogel is injected into a living body through injection, there are still risks of tissue damage and bleeding, and most of conventional hydrogels have insufficient properties and adhesion to be maintained in vivo for a long time.

In order to overcome the limitations of the conventional techniques, such as a risk of tissue damage, user's inconvenience, and cell and drug delivery inefficiency, the present inventors fabricated a hydrogel patch, which is remarkably excellent in drug and cell delivery efficiency and user's convenience, by freeze-drying a hyaluronic acid derivative functionalized with a catechol group or a pyrogallol group.

DISCLOSURE OF THE INVENTION

Problems to be Solved by the Invention

An object of the present disclosure to provide a hydrogel patch having excellent biocompatibility, adhesion, mechanical properties, and convenience in use, and a method for drug delivery, cell transplantation and tissue regeneration using the same.

Means for Solving the Problems

In order to achieve the above object, an aspect of the present disclosure provides a hydrogel patch made of a biocompatible polymer functionalized with a catechol group or a pyrogallol group.

As used herein, the term "catechol group" refers to a functional group derived from a catechol-based compound including 1,2-dihydroxybenzene in which two hydroxy groups (—OH) are located adjacent to each other, and forms covalent crosslinking with various functional groups through oxidation reaction. The catechol-based compound has a broad concept including both catechol and derivatives thereof, and may desirably further include an end functional group for reaction with the biocompatible polymer in addition to the catechol group, but is not limited thereto. The catechol-based compound may be selected from the group consisting of catechol, 4-tert-butylcatechol (TBC), urushiol, alizarin, dopamine, dopamine hydrochloride, 3,4-dihydroxyphenylalanine (DOPA), caffeic acid, norepinephrine (desirably, L-norepinephrine), epinephrine (desirably, L(–)-epinephrine)), 3,4-dihydroxyphenylacetic acid (DOPAC), isoprenaline, isoproterenol (desirably, DL-isoproterenol) and 3,4-dihydroxybenzoic acid. In the present disclosure, as a catechol-based compound, dopamine hydrochloride was used. In that case, —NH$_2$ as an end functional group of the dopamine hydrochloride may react with the biocompatible polymer (particularly, hyaluronic acid).

As used herein, the term "pyrogallol group" refers to a functional group derived from a pyrogallol-based compound including 1,2,3-trihydroxybenzene in which three hydroxy groups (—OH) are adjacent to each other, and forms covalent crosslinking with various functional groups through oxidation reaction. Particularly, the pyrogallol group can be naturally oxidize within minutes without treatment with an oxidant in high oxygen environments, such as in the human body, due to its rapid oxidizing properties. Therefore, when a hydrogel patch is actually applied to clinical practice, it can be directly applied without treatment with an oxidant. The pyrogallol-based compound has a broad concept including both pyrogallol and derivatives thereof, and may desirably further include an end functional group for reaction with the biocompatible polymer in addition to the pyrogallol group, but is not limited thereto. The pyrogallol-based compound may be selected from the group consisting of pyrogallol, 5-hydroxydopamine, tannic acid, gallic acid, epigallocatechin, epicatechin gallate, epigallocatechin gallate, 2,3,4-trihydroxybenzaldehyde, 2,3,4-trihydroxybenzoic acid, 3,4,5-trihydroxybenzaldehyde, 3,4,5-trihydroxybenzamide, 5-tert-butylpyrogallol and 5-methylpyrogallol. In the present disclosure, as a pyrogallol-based compound, 5-hydroxydopamine was used. In that case, —NH$_2$ as an end functional group of the 5-hydroxydopamine may react with the biocompatible polymer (particularly, hyaluronic acid).

As used herein, the term "hydrogel patch" refers to a structure in the form of a thin film having a predetermined thickness and made of a biocompatible polymer, and can be cut into a desired shape for use.

In an embodiment of the present disclosure, the biocompatible polymer may react with an end functional group present in the catechol-based compound or the pyrogallol-based compound so as to be directly functionalized with the catechol group or the pyrogallol group. The biocompatible polymer may be selected from the group consisting of hyaluronic acid, heparin, cellulose, dextran, alginate, chitosan, chitin, collagen, gelatin, chondroitin sulfate, pectin, keratin and fibrin, and may be desirably hyaluronic acid. In that case, —COOH as an end functional group of the hyaluronic acid may react to modify the catechol group or pyrogallol group.

In an embodiment of the present disclosure, a hydrogel patch (hereinafter, referred to as a hydrogel patch) including a biocompatible polymer functionalized with the catechol group or pyrogallol group has a nanofiber-based porous structure and has excellent swelling properties compared with a solution-based hydrogel (hereinafter, referred to as a bulk hydrogel) made of a biocompatible polymer functionalized with the catechol group or pyrogallol group. Therefore, cells or a drug can be effectively loaded on the patch even in an in vivo environment.

Also, the hydrogel patch has excellent mechanical properties and tissue adhesion compared with the bulk hydrogel. Therefore, it is possible to maintain the patch structure for a long time in an in vivo environment, attach the patch to the tissue in vivo for a long time, and increase the cell engraftment efficiency by effectively transplanting cells such as stem cells and organoids.

In an embodiment of the present disclosure, the hydrogel patch may have a thickness of from 0.05 mm to 10.0 mm, desirably of from 0.1 mm to 5.0 mm, and more preferably of from 1.6 mm to 5.0 mm.

In an embodiment of the present disclosure, the hydrogel patch may be prepared by the following processes:

(a) a process of pouring a biocompatible polymer solution functionalized with a catechol group or a pyrogallol group evenly on a flat surface; and (b) a process of freeze-drying the solution at $-0.5°$ C. to $-100°$ C. for 5 hours to 48 hours.

In an embodiment of the present disclosure, the process (a) may be performed by pouring 40 µl, 80 µl or 160 µl of an HA-CA or HA-PG solution into an 8 mm cylindrical mold, and the HA-CA or HA-PG solution may be used at a concentration of from 0.1% to 5% and desirably of from 0.5% to 3%. The amount of the HA-CA or HA-PG solution is required to form a polymer hydrogel patch having a thickness of 0.8 mm, 1.6 mm or 3.2 mm. The thickness of the HA-CA or HA-PG hydrogel patch of the present disclosure can be easily regulated.

In an embodiment of the present disclosure, the process (b) may be performed by freeze-drying the biocompatible polymer solution functionalized with the catechol group or pyrogallol group at $-0.5°$ C. to $-100°$ C. for 5 hours to 48 hours, or desirably by freeze-drying at $-50°$ C. to $-100°$ C. for 12 hours to 36 hours. When the biocompatible polymer solution functionalized with the catechol group or pyrogallol group is freeze-dried, the volume of the solution is decreased and a hydrogel patch in the form of a thin film having a predetermined thickness is formed.

Another aspect of the present disclosure provides a drug delivery system including the hydrogel patch and a drug loaded on the hydrogel patch.

In an embodiment of the present disclosure, the drug may be a protein such as a growth factor, and may be selected from the group consisting of, for example, a vascular endothelial growth factor (VEGF), an epidermal growth factor (EGF), a keratinocyte growth factor (KGF), a growth and differentiation factor, a hepatocyte growth factor (HGF), a platelet-derived growth factor (PDGF), a transforming growth factor (TGF), angiopoietin, erythropoietin, a bone morphogenetic protein (BMP), an insulin-like growth factor, an acidic and basic fibroblast growth factor, a granulocyte-macrophage colony-stimulating factor (GM-CSF), a brain-derived neurotrophic factor, a glial cell-derived neurotrophic factor, a nerve growth factor, a stromal cell-derived factor-1 (SDF-1), a substance P (SP), a hypoxia-inducible factor-1 (HIF-1), a Dickkopf-related protein-1 (DKK-1), an interleukin, pembrolizumab (product name: Keytruda), nivolumab (product name: Opdivo), atezolizumab (product name: Tecentriq), ipilimumab (product name: Yervoy), blinatumomab (product name: Blincyto), trastuzumab (product name: Herceptin), cetuximab (product name: Erbitux) and bevacizumab (product name: Avastin).

Also, the drug may be selected from the group consisting of acemethacin, acrivastine, aldosterone, antazoline, astemizole, azatadine, azelastine, beclomethasone, betamethasone, bromfenac, buclizine, carprofen, cetirizine, chlorophyllin, chlorpheniramine, clemastine, cromolyn, cyclizine, cyproheptadine, dexamethasone, diazolinum, diclofenac, diphenhydramine, ebastine, emedastine, epinastine, etodolac, fenbufen, fenoprofen, fexofenadine, fludrocortisone, flurbiprofen, fluorometholone, hydroxyzine, ibuprofen, indomethacin, ketoprofen, ketorolac tromethamine, ketotifen, levocabastine, levocetirizine, lodoxamide, loratadine, loteprednol, loxoprofen, medrysone, mepivacaine, mequitazine, methdilazine, methapyrilene, nabumetone, naphazoline, naproxen, nedocromil, norastemizole, norvastin, olopatadine, fenidamin, phenylephrine, oxatomide, oxymetazoline, pemirolast, pheniramine, picumast, prednisolone, promethazine, rimexolone, repirinast, montelukast, sulindac, suprofen, zafirlukast, tetrahydrozoline, terfenadine, tiaprofenic acid, tometim, tranilast, triamcinolone, trimeprazine, triprolidine, donepezil, rivastigmine, galantamine, memantine, lidocaine, ketamine, methotrexate, cyclosporine, cisplatinum, capecitabine, oxaliplatin, doxorubicin (product name; Adriamycin), mitomycin-C, daunomycin, epirubicin, tamoxifen, sorafenib, 5-fluorouracil, paclitaxel, dexibuprofen, piroxicam, and pharmaceutically acceptable salts and mixtures thereof.

In an embodiment of the present disclosure, the drug delivery system may further include a material, for example, an oxidant, required for attaching (crosslinking) the hydrogel patch the drug to a target delivery site. A sodium periodate may be used as an oxidant. When the oxidant is applied or sprayed onto the hydrogel patch, the catechol group is oxidized and a crosslinking reaction occurs.

In an embodiment of the present disclosure, the drug may be loaded on the hydrogel patch by mixing the drug with a biocompatible polymer solution functionalized with a catechol group or a pyrogallol group to prepare the hydrogel patch, or by applying the drug onto the hydrogel patch and adding an oxidant to crosslink the drug with the hydrogel patch.

The present inventors mixed an aqueous solution of hyaluronic acid functionalized with a catechol group (HA-CA) with VEGF, and freeze-dried the mixture to prepare an HA-CA hydrogel patch, and then checked the drug release pattern and wound healing effect of the HA-CA hydrogel patch. As a result, it was confirmed that there is no difference in drug effect between the HA-CA hydrogel patch which was prepared containing the drug and the HA-CA hydrogel patch in which the drug was crosslinked after the patch was prepared. Also, it was confirmed that the HA-CA hydrogel patch has an excellent wound healing effect compared with the HA-CA bulk hydrogel.

Further, the present inventors introduced PDGF into the wound of a diabetic mouse by using the HA-PG hydrogel patch, and checked the wound healing effect. As a result, it was confirmed that there is no difference in wound healing effect between the HA-PG hydrogel patch prepared by mixing PDGF in the HA-PG polymer solution in advance and freeze-drying the mixture and the HA-PG hydrogel patch in which PDGF was crosslinked after the patch was prepared. Furthermore, it was confirmed that the wound healing effect was more excellent when PDGF was delivered using the HA-PG hydrogel patch than when it was delivered using the HA-PG bulk hydrogel.

Yet another aspect of the present disclosure provides a method of delivering a drug or cells to a target site, including the following processes:

(a) a process of contacting a drug or cells with the hydrogel patch; and (b) a process of contacting an oxidant with the hydrogel patch of the process (a) optionally when a catechol group is introduced into the hydrogel patch of the process (a).

In an embodiment of the present disclosure, the method of delivering a drug or cells to a target site may be performed by i) attaching the hydrogel patch to the target site and then performing the processes (a) and (b), or ii) contacting the drug or the cells with the hydrogel patch, attaching the hydrogel patch to the target site and then contacting the oxidant with the hydrogel patch, or iii) performing the processes (a) and (b) and then attaching the hydrogel patch loaded with the drug or the cells to the target site.

In an embodiment of the present disclosure, the drug of the process (a) may be the same drug as used in the drug delivery system, and the cells of the process (a) may be selected from the group consisting of stem cells, vascular endothelial cells, osteoblasts, chondrocytes, cardiac cells, muscle cells, keratinocytes, fibroblasts, nerve cells, hepatocytes, intestinal cells, gastric cells, skin cells, adipocytes, blood cells, immune cells, cell spheroids and organoids.

As used herein, the term "cell spheroid" refers to a three-dimensional spherical cellular assembly formed by gathering a plurality of single cells.

As used herein, the term "organoid" refers to a three-dimensional cellular assembly (organ analogue) formed through self-renewal and self-organization of a stem cell, and as a stem cell, an adult stem cell (ASC), an embryonic stem cell (ESC), an induced pluripotent stem cell (iPSC), an adipose-derived stem cell (ADSC), a mesenchymal stem cell (MSC), a placental-derived stem cell (PDSC) or a neural stem cell (NSC) may be used. Stem cells are cultured in three dimensions by mimicking the internal environment of the human body. Thus, the physiological functions of the human body can be similarly reproduced. Also, organ analogues can be constructed from the tissues of a patient, which facilitates disease modeling and drug screening based on genetic information of the patient.

In an embodiment of the present disclosure, the process (b) of contacting an oxidant with the hydrogel patch may be performed by applying or spraying an oxidant solution onto the hydrogel patch to which the drug or cells have been applied.

The present inventors transplanted mesenchymal stem cells into a rat model of ischemic myocardial infarction by the above-described method and found that the transplantation and engraftment efficiency of the mesenchymal stem cells was increased, the heart function was improved and the damaged myocardial tissues were repaired. Also, it was confirmed that the wound recovery and skin tissue regeneration were promoted as a result of introduction of VEGF to the wound on the back of the mouse by the above-described method. Therefore, it is possible to effectively introduce a drug and cells to a target site by the above-described method.

In an embodiment of the present disclosure, the drug delivery system or the method of delivering a drug or cells to a target site may be used for treatment or improvement of Alzheimer's, stroke, Parkinson's disease, epilepsy, cerebral hemorrhage, cerebral infarction, brain tumor, meningitis, spinal cord injury, skin wound, eczema, atopy, shingles, athlete's foot (dermatophytes), seborrheic dermatitis, bedsores, psoriasis, cellulitis, folliculitis, hand-foot-and-mouth disease, herpes, warts, corns, gastrointestinal damage, gastric ulcer, duodenal ulcer, ulcerative colitis, Crohn's disease, bone defect, osteoporosis, cartilage rupture, chondromalacia, muscle injury, ligament/tendon injury, fasciitis, myelofibrosis, arthritis, Grave's disease, lupus, cataract, glaucoma, macular degeneration, retinal injury, liver cirrhosis, alcoholic liver disease (fatty liver), cirrhosis of the liver, kidney failure, silicosis, cystic lung disease, obstructive pulmonary disease, chronic lung disease, pneumonia, pulmonary fibrosis, cystic fibrosis, tonsil stones, bronchiectasis, organ stenosis, vocal cord/laryngeal nodule, periodontitis, stomatitis, herpes labialis, hyperlipidemia, hypercholesterolemia, dyslipidemia, peripheral vascular disease, lower limb ischemia, arteriosclerosis, myocardial fibrosis, myocardial infarction, cardiomyopathy, heart failure, angina, cholangitis, pancreatitis, gastritis, reflux esophagitis, esophageal stenosis, esophagus diverticula, esophageal myoma, idiopathic esophagectasia, Plummer-Vinson syndrome, esophageal varices, hepatitis, otitis media, bronchitis, thyroiditis, conjunctivitis, vasculitis, tonsillitis, spondylitis, pyelonephritis, cystitis, sprain, pleurisy, thyroid cancer, ovarian cancer, cervical cancer, lung cancer, stomach cancer, liver cancer, breast cancer, multiple myeloma, digestive organ cancer, pancreatic cancer, cholelithiasis, gallbladder cancer, biliary tract cancer, colon cancer, prostate cancer, lymphoma, bone and soft tissue cancer, head and neck cancer, blood cancer, esophageal cancer, osteosarcoma, laryngeal cancer, diabetes, diabetic foot ulcer, diabetic retinopathy, diabetic kidney disease, diabetic neuropathy or obesity.

Still another aspect of the present disclosure provides a method of forming a structure inspired by a biological tissue, including:

(a) a process of wrapping a mold of a predetermined shape with a hydrogel patch; and (b) a process of contacting stem cells with the hydrogel patch.

In an embodiment of the present disclosure, the processes (a) and (b) of the method of forming a structure inspired by a biological tissue may be repeated once or more times.

In an embodiment of the present disclosure, the stem cells of the process (b) may be selected from adult stem cells, embryonic stem cells, induced pluripotent stem cells, adipose tissue-derived stem cells, mesenchymal stem cells, placenta-derived stem cells and neural stem cells, but may not be limited thereto.

In an embodiment of the present disclosure, when a catechol group is introduced into the hydrogel patch of the process (a), the process (b) may be performed by applying the stem cells to the hydrogel patch and then contacting an oxidant with the hydrogel patch. Specifically, the process (b) may be performed by dropping or spraying an oxidant solution onto the hydrogel patch. Also, when a pyrogallol group is introduced into the hydrogel patch of the process (a), the process (b) may be performed by applying a solution containing the stem cells to the hydrogel patch.

In an embodiment of the present disclosure, the biological tissue may be blood vessel, skin or liver, but is not limited thereto.

Effects of the Invention

A biocompatible polymer hydrogel patch functionalized with a catechol group or pyrogallol group of the present disclosure has remarkably excellent mechanical properties and adhesion compared with a solution-based bulk hydrogel. Therefore, it can load cells and a drug in vivo for a long time and also safely and efficiently deliver the cells and the drug into the body without damage of the tissue. Further, the biocompatible polymer hydrogel patch functionalized with a catechol group or pyrogallol group is in the form of a thin film having a predetermined thickness and thus is easier to handle and more simple to use than the bulk hydrogel. The biocompatible polymer hydrogel patch functionalized with a catechol group or pyrogallol group can be cut into a desired shape and thus is convenient to use. Furthermore, a mold of a desired shape can be wrapped in one or more layers with the biocompatible polymer hydrogel patch functionalized with a catechol group to form a multi-layered hydrogel patch, and stem cells can be attached thereto to form a structure similar to an in vivo tissue.

In particular, when the hydrogel patch is functionalized with a pyrogallol group, it is naturally oxidized in an in vivo environment without an oxidant. Therefore, it can be conveniently used in actual clinical practice.

BRIEF DESCRIPTION OF THE DRAWINGS

FIG. 6B shows the result of checking the tissue adhesion measured by the measurement method.

FIG. 6C shows the result of checking the tissue adhesion measured by the measurement method.

FIG. 6D shows the result of checking work of tissue adhesion measured by the measurement method.

FIG. 7B shows the result of checking the stainless steel adhesion of the HA-CA hydrogel patch (Patch) and the HA-CA bulk hydrogel (Gel).

FIG. 7C shows the result of checking the work of adhesion of the HA-CA hydrogel patch (Patch) and the HA-CA bulk hydrogel (Gel).

FIG. 11A shows the result of triphenyltetrazolium chloride (TTC) staining of the damaged heart tissue after stem cells are transplanted into a model rat of ischemic myocardial infarction by the HA-CA hydrogel patch (MSC-patch) or injection method (MSC-injection).

FIG. 11B shows the result of triphenyltetrazolium chloride (TTC) staining of the damaged heart tissue after stem cells are transplanted into a model rat of ischemic myocardial infarction by the HA-CA hydrogel patch (MSC-patch) or injection method (MSC-injection).

FIG. 11C shows the result of Masson's Trichrome staining of the damaged heart tissue after stem cells are transplanted into a model rat of ischemic myocardial infarction by the HA-CA hydrogel patch (MSC-patch) or injection method (MSC-injection).

FIG. 11D shows the result of Masson's Trichrome staining of the damaged heart tissue after stem cells are transplanted into a model rat of ischemic myocardial infarction by the HA-CA hydrogel patch (MSC-patch) or injection method (MSC-injection).

FIG. 14A shows the result of fabrication of a multi-layered HA-CA hydrogel patch (A) and the result of mimicking a multi-layered in vivo structure using the same (B).

FIG. 14B shows the result of fabrication of a multi-layered HA-CA hydrogel patch (A) and the result of mimicking a multi-layered in vivo structure using the same (B).

FIG. 15A shows the result of fabrication of a multi-layered HA-CA hydrogel patch in the form of a tube.

FIG. 15B shows the result of fabrication of a multi-layered HA-CA hydrogel patch in the form of a tube.

FIG. 18A shows the result of checking the hair follicle regeneration after a vascular endothelial growth factor (VEGF) is introduced into a mouse wound model by using the HA-CA hydrogel patch.

FIG. 18B shows the result of checking the collagen production after a vascular endothelial growth factor (VEGF) is introduced into a mouse wound model by using the HA-CA hydrogel patch.

FIG. 18C shows the result of checking the hair follicle regeneration after a vascular endothelial growth factor (VEGF) is introduced into a mouse wound model by using the HA-CA hydrogel patch.

FIG. 18D shows the result of checking the collagen production after a vascular endothelial growth factor (VEGF) is introduced into a mouse wound model by using the HA-CA hydrogel patch.

FIG. 18E shows the result of checking the degree of blood vessel formation after a vascular endothelial growth factor (VEGF) is introduced into a mouse wound model by using the HA-CA hydrogel patch.

FIG. 18F shows the result of checking the degree of blood vessel formation after a vascular endothelial growth factor (VEGF) is introduced into a mouse wound model by using the HA-CA hydrogel patch.

FIG. 19A shows the result of checking the wound healing efficacy after a drug is introduced into a mouse wound model by using the HA-CA hydrogel patch or the HA-CA bulk hydrogel.

FIG. 19B shows the result of checking the wound healing efficacy after a drug is introduced into a mouse wound model by using the HA-CA hydrogel patch or the HA-CA bulk hydrogel.

FIG. 22 shows the result of checking the cytotoxicity of an HA-PG hydrogel patch (Patch (PG)) and an HA-PG bulk hydrogel (Gel (PG)).

FIG. 23A shows the result of checking the swelling ratio of an HA-PG hydrogel patch (Patch (PG)) and an HA-PG bulk hydrogel (Gel (PG)).

FIG. 23B shows the result of checking the swelling ratio of an HA-PG hydrogel patch (Patch (PG)) and an HA-PG bulk hydrogel (Gel (PG)).

FIG. 23C shows the result of checking the degradation ratio in hyaluronidase.

FIG. 24 shows the result of checking the internal structure of the HA-PG hydrogel patch (Patch (PG)) and the HA-PG bulk hydrogel (Gel (PG)) under a scanning electron microscope.

FIG. 25A shows the result of checking the mechanical strength of the HA-PG hydrogel patch (Patch (PG)) and the HA-PG bulk hydrogel (Gel (PG)).

FIG. 25B shows the result of checking the mechanical strength of the HA-PG hydrogel patch (Patch (PG)) and the HA-PG bulk hydrogel (Gel (PG)).

FIG. 25C shows the result of checking the elastic modulus depending on the thickness of the HA-PG hydrogel patch.

FIG. 26A shows the result of checking the tissue adhesion of the HA-PG hydrogel patch (Patch (PG)) and the HA-PG bulk hydrogel (Gel (PG)).

FIG. 26B shows the result of checking the tissue adhesion of the HA-PG hydrogel patch (Patch (PG)) and the HA-PG bulk hydrogel (Gel (PG)).

FIG. 26C shows the result of checking the work of tissue adhesion of the HA-PG hydrogel patch (Patch (PG)) and the HA-PG bulk hydrogel (Gel (PG)).

BEST MODE FOR CARRYING OUT THE INVENTION

Hereafter, one or more specific examples will be described in more detail. However, these examples are provided for illustrative purposes only and the scope of the present disclosure is not limited to these examples.

Preparation Example 1

(1) Fabrication of HA-CA Hydrogel Patch

A dopamine hydrochloride-functionalized hyaluronic acid (hereinafter, referred to as HA-CA) was dissolved in distilled water at a concentration of 1%, and 40 μl, 80 μl or 160 μl of the 1% HA-CA solution was poured into an 8 mm cylindrical mold and then freeze-dried overnight at −80° C. to prepare HA-CA hydrogel patches with thicknesses of 0.8 mm, 1.6 mm, and 3.2 mm, respectively. The prepared HA-CA hydrogel patches are in a dry state and thus are easy to store. Also, they are fabricated in the form of a thin film and thus can be easily cut into a desired shape. Therefore, they are convenient to use.

The HA-CA hydrogel patch cut into a specific shape was placed on the surface of a target tissue, and a desired drug or cells were applied onto the patch. Thereafter, a sodium periodate ($NaIO_4$; oxidant) was sprayed onto the HA-CA hydrogel patch to encapsulate the cells or drug in the patch.

In a previous test, when the concentration of HA-CA is higher than 1%, the hydrogel patch is so hard that the cells and drug cannot effectively penetrate into the hydrogel patch, and when the concentration of HA-CA is low, the structure of the hydrogel patch is not sufficiently maintained and the cells and drug are lost. Also, when the HA-CA hydrogel patch is too thick, the cells and drug cannot effectively penetrate into the hydrogel patch, and when the HA-CA hydrogel patch is too thin, it is difficult to handle the hydrogel patch and the structure of the hydrogel patch cannot be maintained for a long time after an oxidant is applied.

In Examples 1-1 to 1-5, an HA-CA hydrogel patch with a thickness of 1.6 mm was used.

Figure 1A:
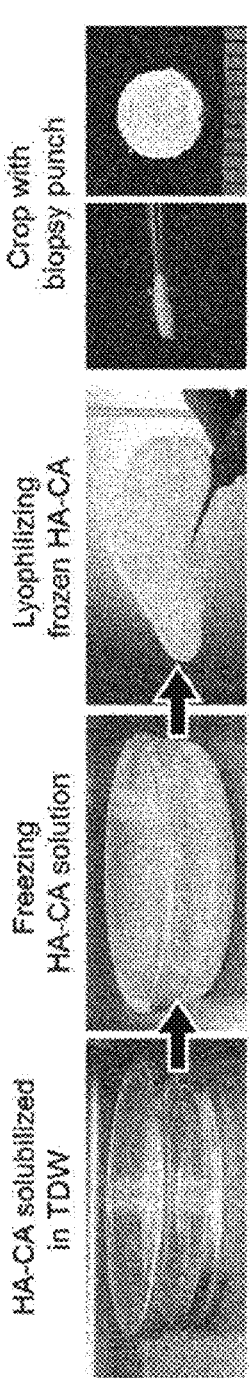
FIG. 1A schematically illustrates a process of fabricating a catechol-functionalized hyaluronic acid (HA-CA) hydrogel patch (A).
Figure 1B:
FIG. 1B schematically illustrates a HA-CA hydrogel patches with different thicknesses (B).
Figure 1C:
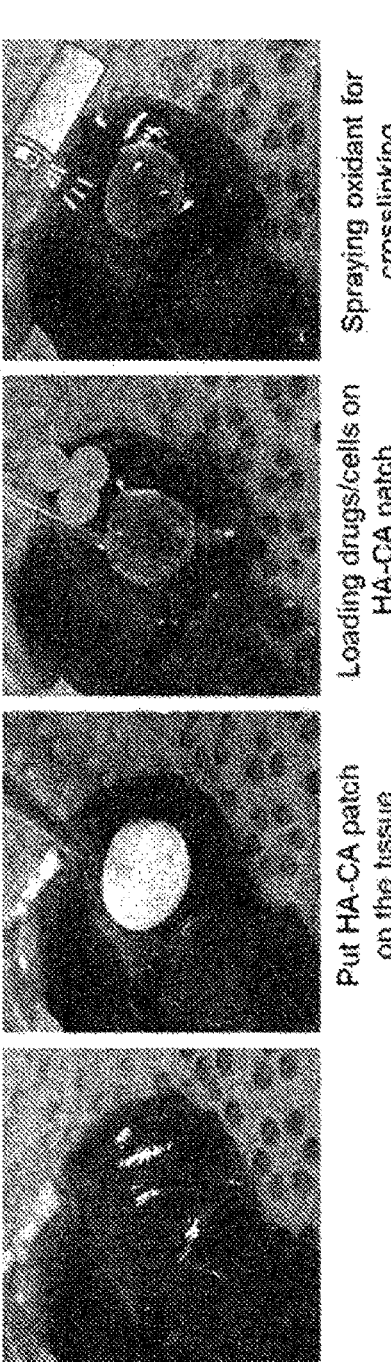
FIG. 1C schematically illustrates a method of using the hydrogel patch (C).

FIG. 1A shows a process of fabricating an HA-CA hydrogel patch, FIG. 1B shows HA-CA hydrogel patches with different thicknesses, and FIG. 1C schematically shows a method of using the HA-CA hydrogel patch.

(2) Fabrication of HA-CA Bulk Hydrogel

HA-CA was dissolved in phosphate-buffered saline (PBS), and a sodium periodate solution was added into the solution (HA-CA solution:oxidant solution=3:1 (v/v)) to prepare an HA-CA bulk hydrogel. A final concentration of HA-CA in the prepared HA-CA bulk hydrogel was 2%. The prepared HA-CA bulk hydrogel was used for analyzing the structure and cytotoxicity. The HA-CA bulk hydrogel including a drug or cells was prepared by mixing the HA-CA solution with the drug or cells in advance and adding the sodium periodate solution thereto.

Example 1-1: Characterization of HA-CA Hydrogel Patch (1) Check on Cytotoxicity

The HA-CA hydrogel patch or the HA-CA bulk hydrogel prepared in Preparation Example was placed on the bottom of a 6-well cell culture plate, and human adipose-derived stem cells (hADSCs) were dispensed and cultured for 7 days. The cell viability was checked using Live/Dead assay (Invitrogen; USA) according to the manufacturer's protocol on 0, 3, and 7 days of culture.

Figure 2A:
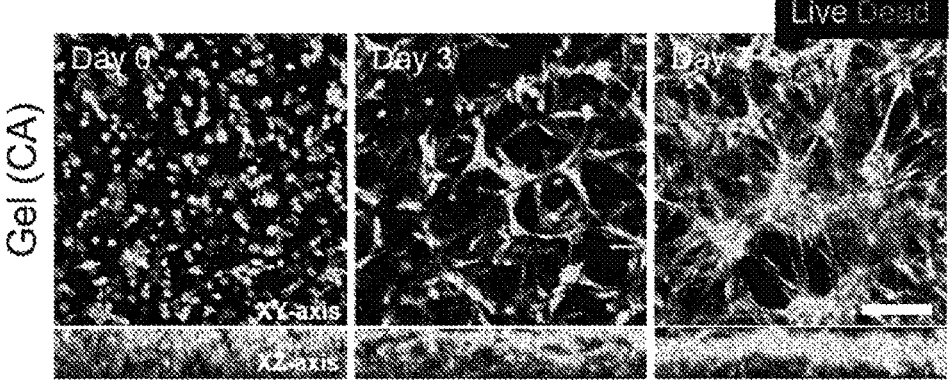
FIG. 2A shows the result of checking the cytotoxicity and three-dimensional culture of an HA-CA bulk hydrogel.
Figure 2B:
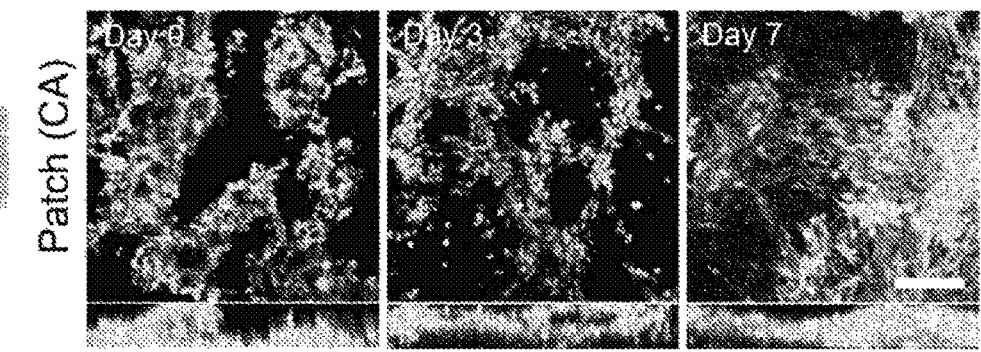
FIG. 2B shows the result of checking the cytotoxicity and three-dimensional culture of an HA-CA hydrogel patch.

As a result, it was found that the HA-CA bulk hydrogel whose biocompatibility was already verified had no cytotoxicity (FIG. 2A) and the HA-CA hydrogel patch also had no cytotoxicity (FIG. 2B). In addition, as shown in the XZ axis images, it was found that the cells were distributed in the HA-CA hydrogel patch not in a single layer but in three dimensions. This result means that even when the form of the HA-CA bulk hydrogel was modified into an HA-CA hydrogel patch, the biocompatibility of hyaluronic acid was maintained and three-dimensional culture of cells was also possible.

(2) Check on Swelling Ratio and Degradation Ratio

Figure 3A:
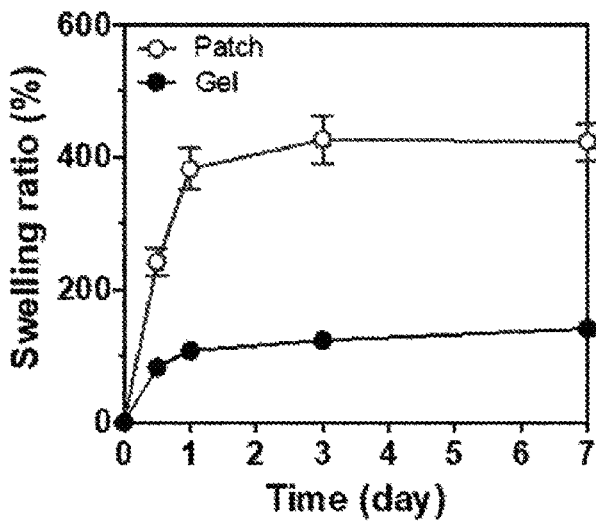
FIG. 3A shows the result of checking the swelling ratio of an HA-CA hydrogel patch (Patch) and an HA-CA bulk hydrogel (Gel).
Figure 3B:
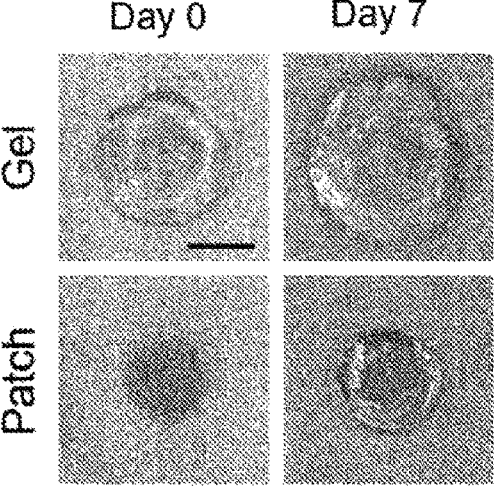
FIG. 3B shows the result of checking the swelling ratio of an HA-CA hydrogel patch (Patch) and an HA-CA bulk hydrogel (Gel).
Figure 3C:
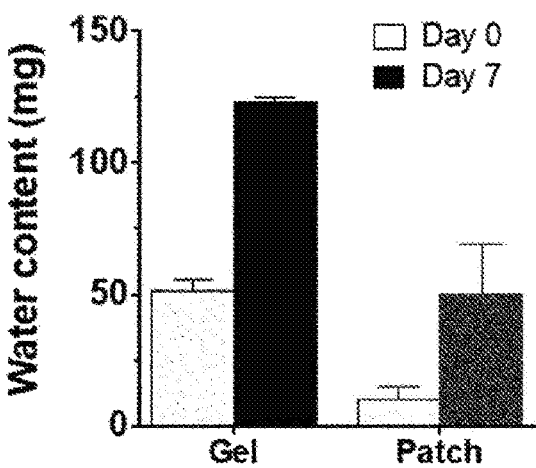
FIG. 3C shows the result of checking the water content of an HA-CA hydrogel patch (Patch) and an HA-CA bulk hydrogel (Gel).

An HA-CA hydrogel patch or an HA-CA bulk hydrogel was immersed in PBS at 37° C. similar to in vivo conditions for 7 days, and the swelling ratio was measured after 12 hours, 1 day, 3 days and 7 days. As a result of measurement, the swelling ratio of the HA-CA hydrogel patch was about 4 times higher than that of the HA-CA bulk hydrogel (FIG. 3A), and the actual water content was higher in the HA-CA bulk hydrogel than in the HA-CA hydrogel patch. (FIG. 3B and FIG. 3C).

Figure 3D:
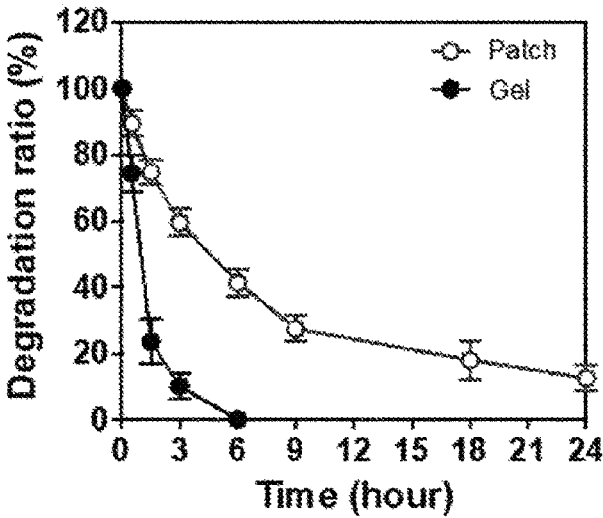
FIG. 3D shows the result of checking the degradation ratio of an HA-CA hydrogel patch (Patch) and an HA-CA bulk hydrogel (Gel) after hyaluronidase treatment.

Since various degrading enzymes exist in the actual in vivo environment, the HA-CA hydrogel patch or the HA-CA bulk hydrogel was immersed in PBS at 37° C. and then treated with a hyaluronidase until degradation. The weights of the HA-CA hydrogel patch and the HA-CA bulk hydrogel were measured at regular time intervals to measure the degrees of degradation over time. As a result of measurement, the HA-CA bulk hydrogel was rapidly degraded within 2 hours after treatment with a hyaluronidase and completely degraded after 6 hours. The HA-CA hydrogel patch remained even after 24 hours from the treatment with a hyaluronidase. Thus, it was found that the rate of degradation of the HA-CA hydrogel patch is slower than that of HA-CA bulk hydrogel (FIG. 3D).

(3) Check on Internal Structure

Figure 4:
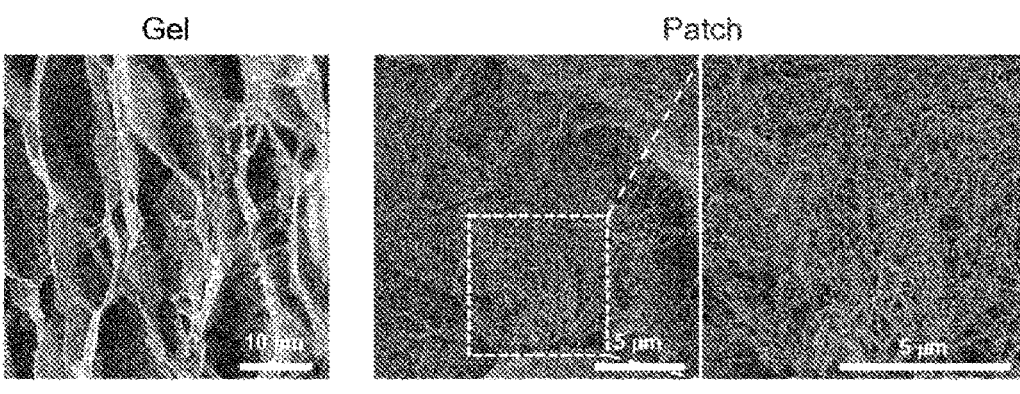
FIG. 4 shows the result of checking the internal structure of the HA-CA bulk hydrogel (Gel) and the HA-CA hydrogel patch (Patch) under a scanning electron microscope.

The internal structures of the HA-CA hydrogel patch and the HA-CA bulk hydrogel were examined under a scanning electron microscope. As a result, it was confirmed that the HA-CA bulk hydrogel had a porous structure of micrometer (μm) size, whereas the HA-CA hydrogel patch had a nano-fiber-based porous structure (FIG. 4). This result means that the HA-CA hydrogel patch has a denser internal structure than the HA-CA bulk hydrogel and the surface area functionalized with catechol is increased by the nanofiber structure, and, thus, the tissue adhesion becomes excellent.

(4) Measurement of Mechanical Strength

Figure 5A:
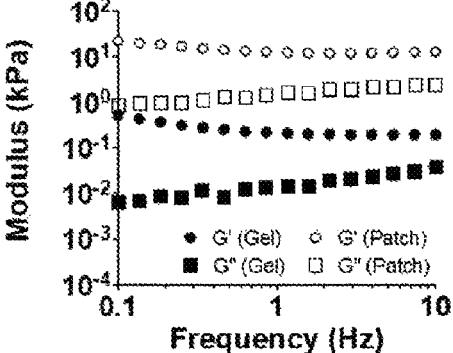
FIG. 5A shows the result of checking the mechanical strength of the HA-CA hydrogel patch (Patch) and the HA-CA bulk hydrogel (Gel).

The elastic moduli of the HA-CA hydrogel patch and the HA-CA bulk hydrogel were measured at a frequency of from 0.1 Hz and 10 Hz by using a rheometer. As a result of measurement, both the HA-CA hydrogel patch and the HA-CA bulk hydrogel showed higher G' values than G" values. Thus, it was found that the internal structure is formed of a stable polymer network (FIG. 5A).

Figure 5B:
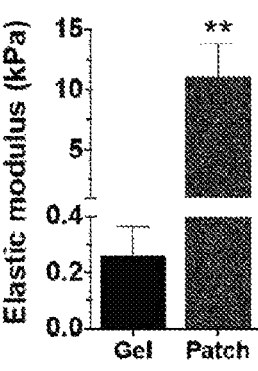
FIG. 5B shows the result of checking the mechanical strength of the HA-CA hydrogel patch (Patch) and the HA-CA bulk hydrogel (Gel).
Figure 5C:
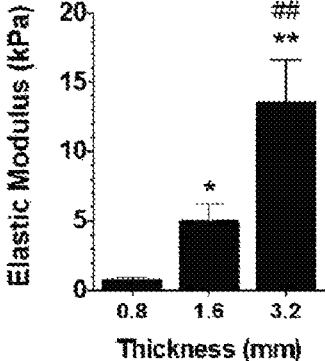
FIG. 5C shows the result of checking of the elastic modulus depending on the thickness of the HA-CA hydrogel patch.

Further, the average elastic modulus of the HA-CA bulk hydrogel was about 260 Pa, whereas the elastic modulus of the HA-CA hydrogel patch was about 11 kPa. Thus, it was found that the elastic modulus increased by about 50 times or more (FIG. 5B). As a result of measuring the elastic modulus of the HA-CA hydrogel patch prepared in Preparation Example 1, it was found that the elastic modulus significantly increased from 0.8 kPa to 5 and 14 kPa as the thickness of the patch increased (FIG. 5C). The increase in the elastic modulus means that the mechanical strength becomes excellent.

The above test results mean that the HA-CA hydrogel patch has a remarkably higher mechanical strength than the HA-CA bulk hydrogel and the mechanical strength of the HA-CA hydrogel patch can be easily regulated by regulating the thickness of the HA-CA hydrogel patch.

(5) Measurement of Living Tissue Adhesion

Figure 6A:
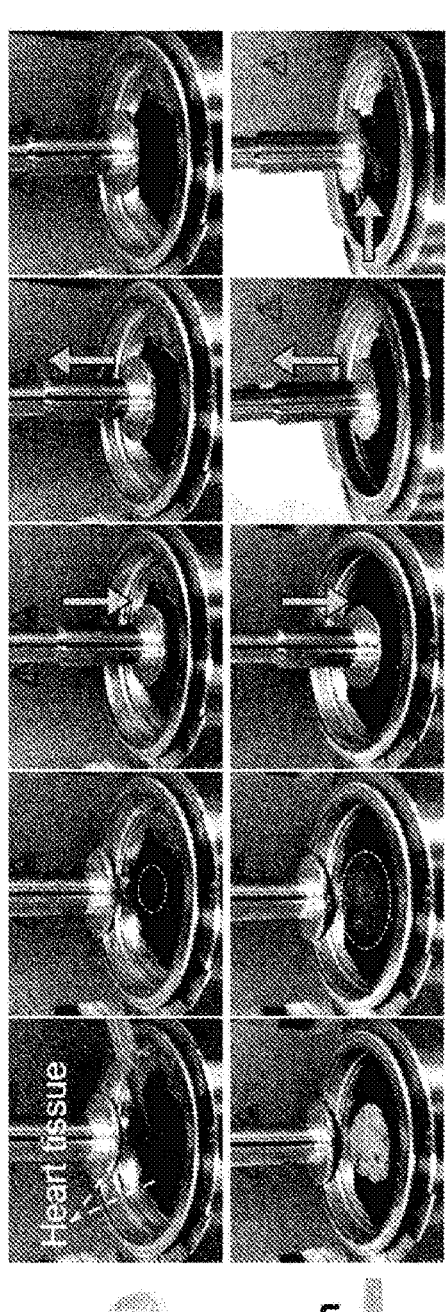
FIG. 6A shows a method of measuring the tissue adhesion of the HA-CA hydrogel patch (Patch) and the HA-CA bulk hydrogel (Gel).

After the HA-CA hydrogel patch was placed on the pig heart tissue, an oxidant was sprayed or the HA-CA bulk hydrogel in which crosslinking was induced by mixing the oxidant was placed on the pig heart tissue. Then, the HA-CA hydrogel patch was pressed by a probe attached with the pig heart tissue and then left for 10 minutes. Thereafter, the tissue adhesions of the HA-CA hydrogel patch and the HA-CA bulk hydrogel was measured using an adhesion meter (FIG. 6A).

As a result of measurement, it was found that the HA-CA bulk hydrogel had an adhesion of about 1.5 N, whereas the HA-CA hydrogel patch had an adhesion of about 5.5 N, indicating that the tissue adhesion was improved by 3.5 times or more (FIG. 6B and FIG. 6C).

Further, the area of the adhesion-extension length graph (FIG. 6B) was measured to calculate the amount of work (work of adhesion) required to separate the HA-CA bulk hydrogel or hydrogel patch attached to the pig heart tissue. As a result, it was found that the work of adhesion of the HA-CA hydrogel patch increased by 8 times or more compared with the HA-CA bulk hydrogel (FIG. 6D).

(6) Measurement of Adhesion (Stainless Steel Surface)

The HA-CA hydrogel patch or the HA-CA bulk hydrogel was placed on the surface of stainless steel, and the adhesion was measured in the same manner as in Test Example 1-5 described above.

Figure 7A:
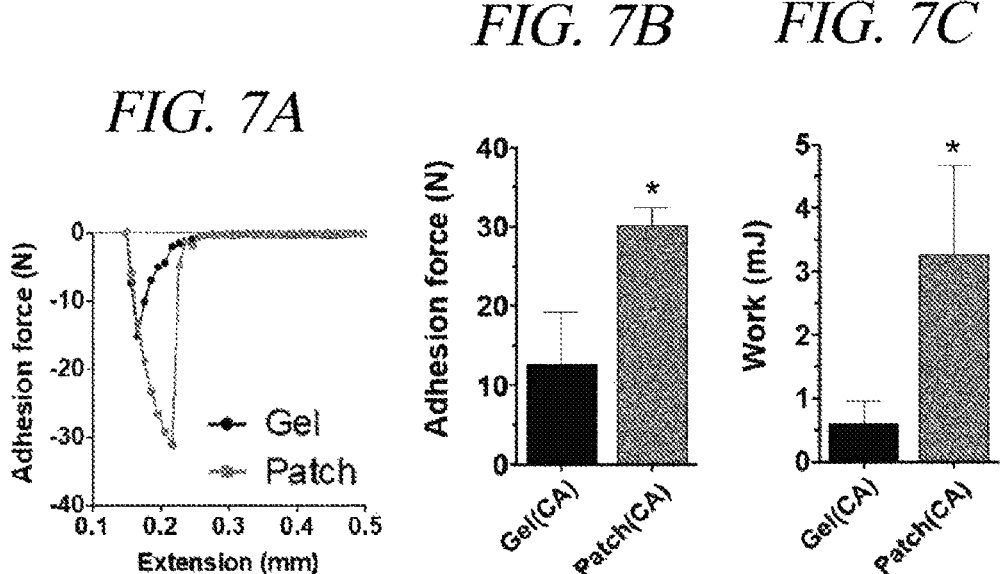
FIG. 7A shows the result of checking the stainless steel adhesion of the HA-CA hydrogel patch (Patch) and the HA-CA bulk hydrogel (Gel).

As a result of measurement, it was found that the HA-CA bulk hydrogel had an adhesion of about 12 N, whereas the HA-CA hydrogel patch had an adhesion of about 30 N, indicating that the adhesion was improved by 2.5 times or more (FIG. 7A and FIG. 7B).

Further, the area of the adhesion-extension length graph (FIG. 7A) was measured to calculate the work of adhesion required to separate the HA-CA bulk hydrogel or hydrogel patch attached to the surface of stainless steel. As a result, it was found that the work of adhesion of the HA-CA hydrogel patch increased by 5.5 times or more compared with the HA-CA bulk hydrogel (FIG. 7C).

Example 1-2: Check on Long-Term Adhesion Ability of HA-CA Hydrogel Patch

Figure 8:
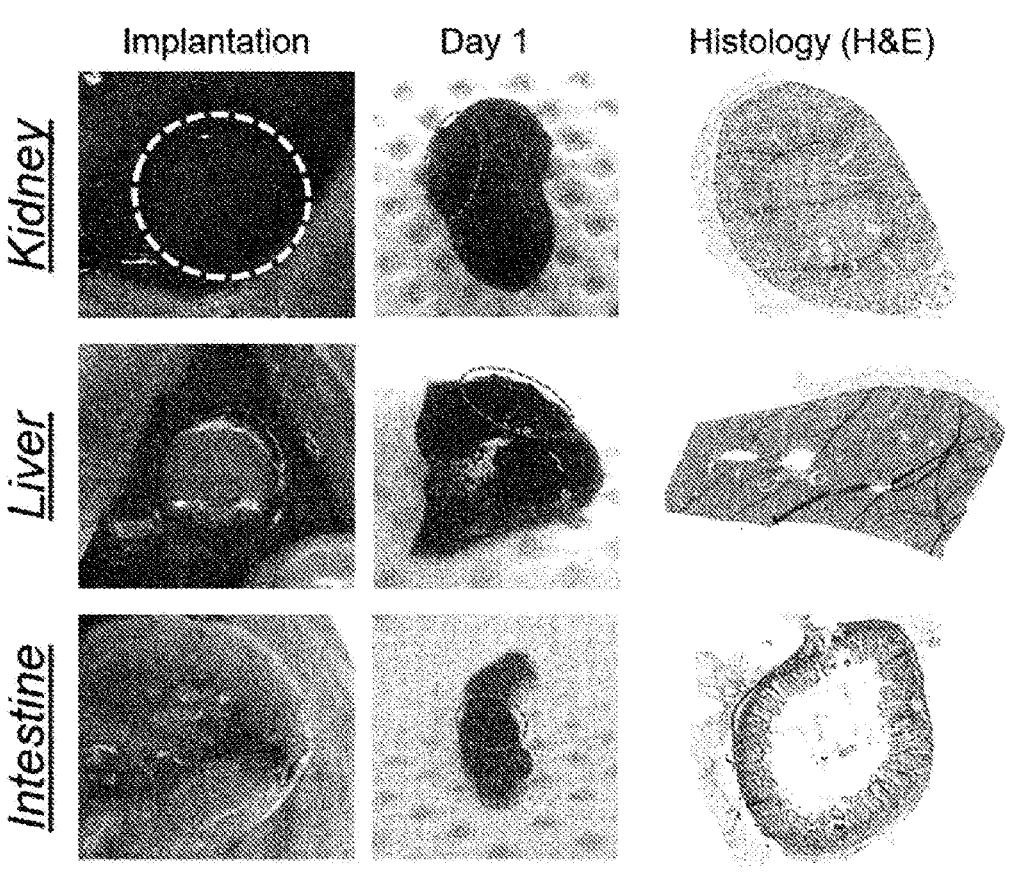
FIG. 8 shows the result of checking whether the adhesion of an HA-CA hydrogel patch is maintained and whether stem cells are engrafted after the stem cells are transplanted into the kidney, liver and intestine using the HA-CA hydrogel patch.

Since the in vivo environment is high in water content, it was checked whether the HA-CA hydrogel patch of the present disclosure can be attached to various organs. After a mouse was anesthetized, the HA-CA hydrogel patch was placed on the kidney, liver and intestine by abdominal incision. Then, human adipose-derived stem cells (hADSCs) were dropped and an oxidant was sprayed, followed by suturing. After 24 hours, the mouse was sacrificed to separate the kidney, liver and intestine. After a visual check on whether the HA-CA hydrogel patch was attached, a tissue section was prepared and stained with hematoxylin and eosin. As a result, it was found that the HA-CA hydrogel patch was attached well to the surface of the organ with high water content even after 24 hours. The tissue staining result shows that the HA-CA hydrogel patch was attached to the kidney, liver and intestine (FIG. 8).

This result means that the HA-CA hydrogel patch can be attached to various organs and tissues in vivo so that non-invasive cell transplantation into various organs and tissues is possible.

Example 1-3: HA-CA Hydrogel Patch Efficacy in Treating Myocardial Infarction (1) Check on Stem Cell Transplantation and Engraftment Efficiency Conventional stem cell transplantation is mainly performed through direct injection into the damaged tissue, and thus has disadvantages of massive loss and poor engraftment of stem cells and risks of bleeding and tissue damage caused by injection. However, the stem cell transplantation method using an adhesive patch has advantages of being able to effectively transplant stem cells into a large tissue area non-invasively. Therefore, the result was confirmed after stem cells were transplanted using the HA-CA hydrogel patch of the present disclosure.

Figure 9A:
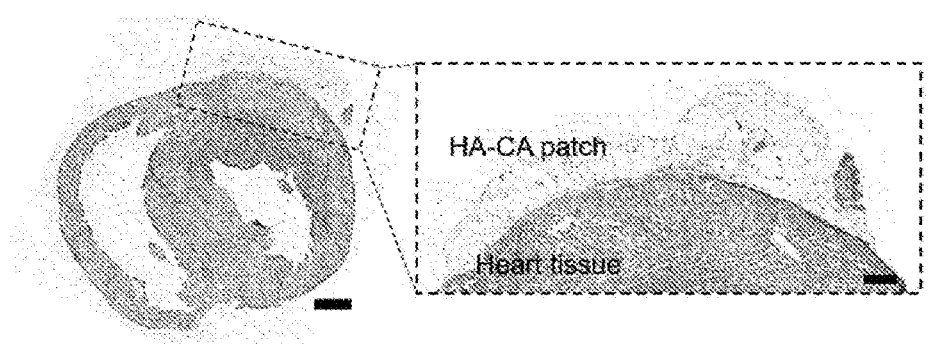
FIG. 9A shows the result of checking whether stem cells are engrafted after the stem cells are transplanted into the myocardial infarction-induced ischemic tissue by an HA-CA hydrogel patch (MSC-patch) or injection method (MSC-injection).

After a model rat of ischemic myocardial infarction was anesthetized, the chest was opened. Then, the HA-CA hydrogel patch was placed on the heart and $2\times10^5$ rat bone marrow-derived mesenchymal stem cells (hereinafter, referred to as "MSC") were dropped. Thereafter, an oxidant was sprayed on the HA-CA hydrogel patch to encapsulate MSC in the HA-CA hydrogel patch. The surgical site was sutured, and the heart tissue in which myocardial infarction occurred on the third day of MSC transplantation was extracted and then stained with hematoxylin and eosin according to a method known in the art. As a result of staining, it was confirmed that the HA-CA hydrogel patch (MSC-patch) containing MSCs was firmly attached to the surface of the heart tissue (FIG. 9A). This result shows that the HA-CA hydrogel patch can be stably attached to the surface of the beating heart and the adhesion can be maintained.

Figure 9B:
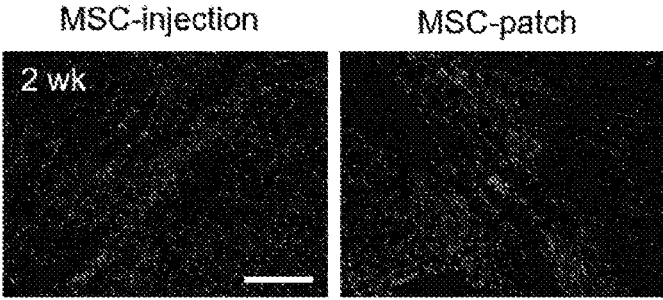
FIG. 9B shows the result of checking whether stem cells are engrafted after the stem cells are transplanted into the myocardial infarction-induced ischemic tissue by an HA-CA hydrogel patch (MSC-patch) or injection method (MSC-injection).

Also, MSCs labeled with a fluorescent material (Paul Karl Horan 26, PKH26) were directly injected into the rat or transplanted into the rat by using the HA-CA hydrogel patch in the same manner as described above. As a result of follow-up 2 weeks after MSC transplantation, it was confirmed that MSCs transplanted on the outer wall of the heart using the HA-CA hydrogel patch migrated into the damaged heart tissue. The engraftment and migration efficiency of MSCs was remarkably higher when using the HA-CA hydrogel patch (MSC-patch) than when using the conventional MSC transplantation (MSC-injection) through direct injection (FIG. 9B).

(2) Evaluation of Cardiac Functionality Through Echocardiography

After model rats of ischemic myocardial infarction were anesthetized, left ventricular coronary artery ligation was performed to induce acute myocardial infarction. Thereafter, the rats were divided into the following groups and compared in terms of healing effect on myocardial infarction: Control Group (saline injection, Saline); Test Group 1 (HA-CA hydrogel patch only, Patch only); Test Group 2 (MSC transplantation by direct injection, MSC-injection); and Test Group 3 (MSC implantation using HA-CA hydrogel patch, MSC-patch). 4 weeks after test, echocardiography was performed to evaluate the effect of improving heart function.

Figure 10A:
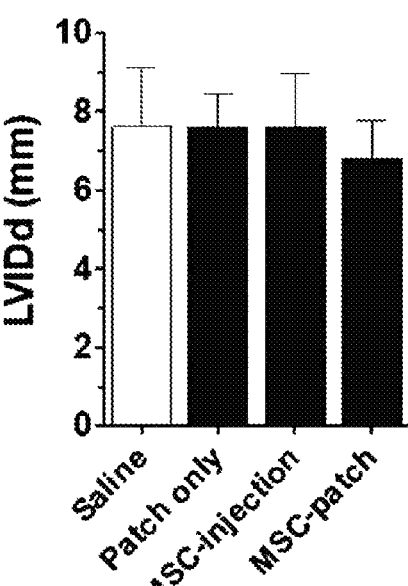
FIG. 10A shows the result of checking the left ventricular end-diastolic diameter, after stem cells are transplanted into a model rat of ischemic myocardial infarction by the HA-CA hydrogel patch (MSC-patch) or injection method (MSC-injection).
Figure 10B:
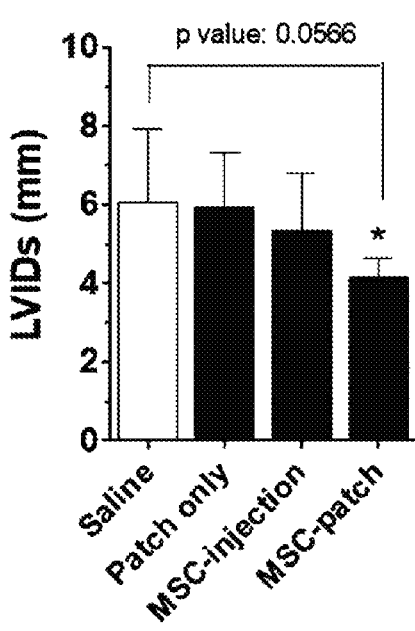
FIG. 10B shows the result of checking the left ventricular end-systolic diameter after stem cells are transplanted into a model rat of ischemic myocardial infarction by the HA-CA hydrogel patch (MSC-patch) or injection method (MSC-injection).
Figure 10C:
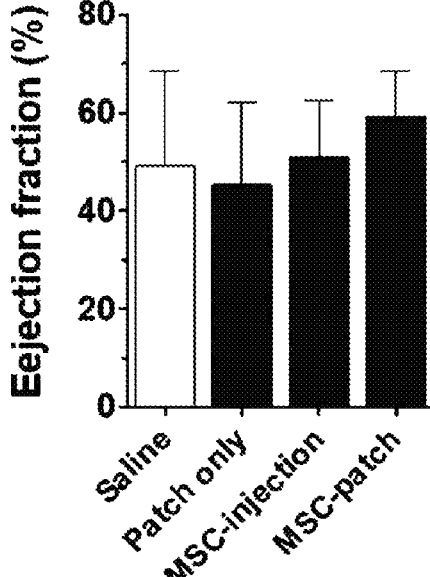
FIG. 10C shows the result of checking the heart ejection fraction after stem cells are transplanted into a model rat of ischemic myocardial infarction by the HA-CA hydrogel patch (MSC-patch) or injection method (MSC-injection).
Figure 10D:
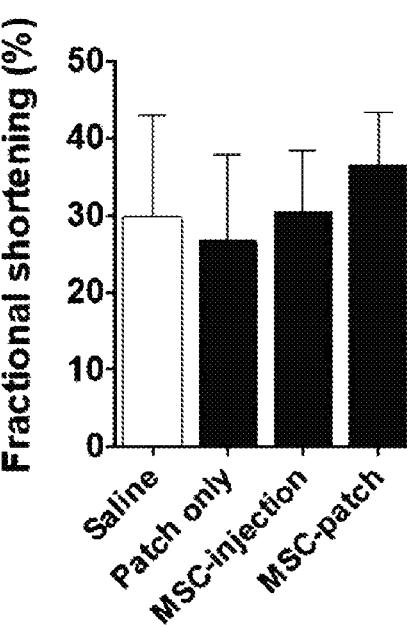
FIG. 10D shows the result of checking the fractional shortening after stem cells are transplanted into a model rat of ischemic myocardial infarction by the HA-CA hydrogel patch (MSC-patch) or injection method (MSC-injection).

As a result of evaluation, it was found that the left ventricle end-systolic dimensions (LVIDs) significantly decreased in Test Group 3 compared with those of Control Group, which means that MSCs transplanted using the HA-CA hydrogel patch effectively reduced damage to the heart tissue to suppress hypertrophy of the ischemic heart (FIG. 10B). It was also found that the ejection fraction, which is an index for evaluating the contractile function of the heart, was also improved in Test Group 3 compared with Control Group (FIG. 10C). Further, the left ventricular fractional shortening was improved in Test Group 3 compared with Control Group (FIG. 10D).

It was confirmed through this test result that MSCs can be transplanted using the HA-CA hydrogel patch and can effectively treat ischemic myocardial infarction.

(3) Examination on Ischemic Tissue Through Histological Analysis

A histological analysis of the damaged heart was performed to check whether MSCs transplanted using the HA-CA hydrogel patch regenerate the damaged myocardial tissue. TTC staining (2,3,5-Triphenyltetrazolium chloride) stains only normal myocardial tissues in red, but an area where the tissue is necrosed due to myocardial infarction is not stained and looks white.

After completion of Test Example 3-2, the rat was anesthetized and the myocardial tissue was separated to make a tissue section slide, and then TTC staining was performed according to a method known in the art. As a result, it was found that any white part was hardly seen in Test Group 3 (MSC-patch) and the infarct size was significantly decreased compared with Control Group (Saline). Meanwhile, it was found that Test Group 1 (Patch only) in which MSCs were not even transplanted exhibited a similar level of tissue necrosis inhibitory effect to Test Group 2 (MSC-injection) (FIG. 11A and FIG. 11B).

Further, the myocardial infarction-induced heart was separated from the rat and then, a tissue section was made. Masson's Trichrome staining was performed to check the degree of fibrosis of the heart tissue caused by ischemia. As a result, it was confirmed that the fibrosis inhibitory effect of Test Group 3 was remarkably excellent and the normal myocardial tissue was well maintained. Test group 2 also exhibited a significant fibrosis inhibitory effect compared with Control Group (FIG. 11C and FIG. 11D).

It was confirmed through this test result that the HA-CA hydrogel patch itself promotes the migration and engraftment of cells in vivo, which is helpful for tissue regeneration, and provides a space for cells to survive and thus can reduce damage to myocardial tissue caused by ischemic disease to a significantly better level than the direct injection of MSCs. Further, it was found that since the transplantation and engraftment efficiency of MSCs was excellent, the HA-CA hydrogel patch can be applied very effectively to the actual treatment of heart disease.

(4) Check on Whether Blood Vessel is Regenerated

It was checked whether MSCs transplanted using the HA-CA hydrogel patch regenerate blood vessels. Specifically, the heart tissue section slide described in paragraph (3) was stained with an arterial specific marker (smooth muscle actin (SMA)) and a capillary marker (CD31).

Figure 12A:
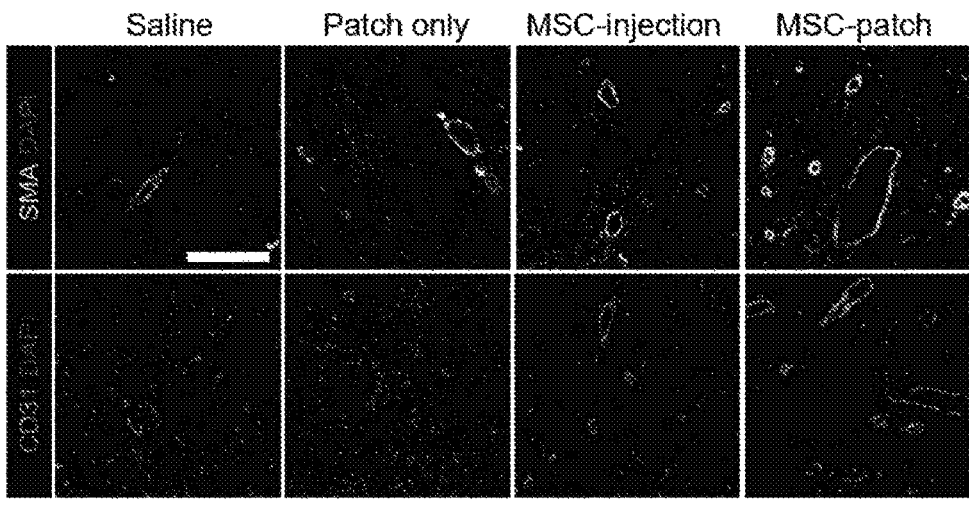
FIG. 12A shows the result of staining a damaged site with an arterial specific marker (smooth muscle actin (SMA)) and a capillary marker (CD31) after stem cells are transplanted into a model rat of ischemic myocardial infarction by the HA-CA hydrogel patch (MSC-patch) or injection method (MSC-injection).
Figure 12B:
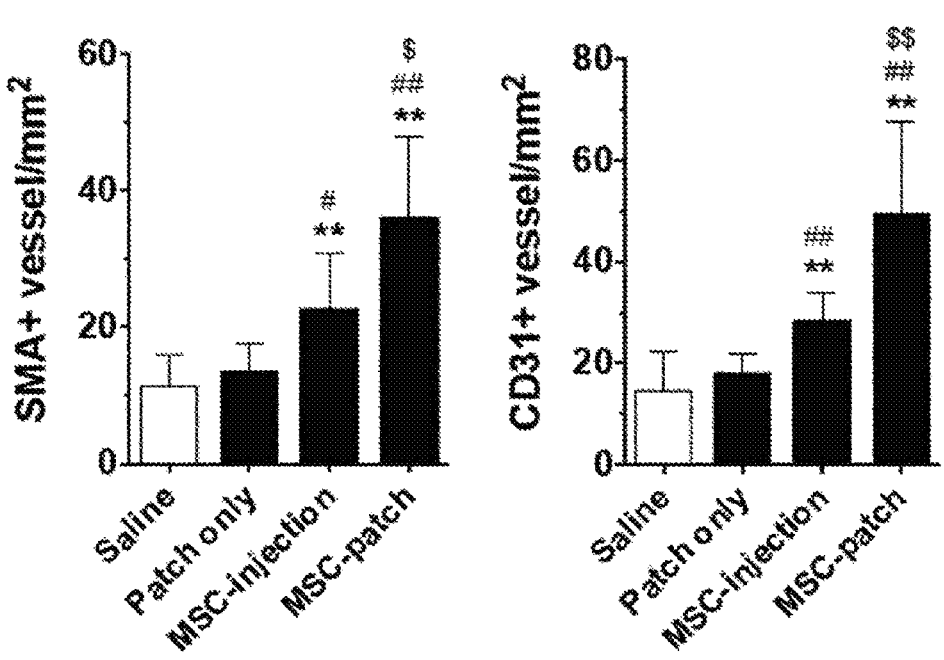
FIG. 12B shows the result of staining a damaged site with an arterial specific marker (smooth muscle actin (SMA)) and a capillary marker (CD31) after stem cells are transplanted into a model rat of ischemic myocardial infarction by the HA-CA hydrogel patch (MSC-patch) or injection method (MSC-injection).

As a result of staining, it was confirmed that the arterioles and capillaries were regenerated remarkably in Test Group 3 (MSC-patch) compared with in Control Group (FIG. 12A and FIG. 12B). This result shows that the MSC transplantation method using the HA-CA hydrogel patch is remarkably more effective in revascularization than the conventional MSC injection method.

Example 1-4: HA-CA Hydrogel Patch Efficacy in Cell Transplantation and Tissue Regeneration (1) Transplantation of Organoid In the conventional method of injecting cells, it is difficult to efficiently transplant large cell masses such as cell spheroids or organoids. This is because a cell structure is destroyed and cells are killed by the pressure when passing through the injection needle during transplantation. Therefore, cell organoid transplantation was performed using the HA-CA hydrogel patch of the present disclosure.

After a mouse was anesthetized, the abdomen was cut open. Then, cell organoids labeled with DiI fluorescence were placed on the surfaces of the liver, stomach and small intestine, and the HA-CA hydrogel patch in the form of a tape was attached to fix the organoids on the surface of each organ.

Figure 13A:
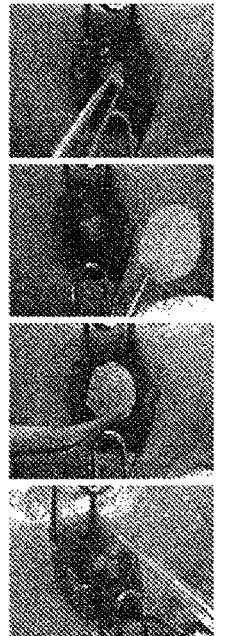
FIG. 13A shows the result of checking whether organoids are engrafted after fluorescent material-labeled organoids are transplanted into the liver by using the HA-CA hydrogel patch.
Figure 13B:
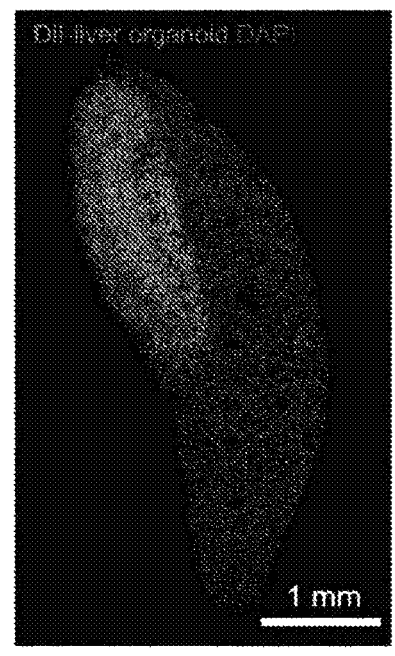
FIG. 13B shows the result of checking whether organoids are engrafted after fluorescent dye-labeled organoids are transplanted into the liver by using the HA-CA hydrogel patch.

The stomach and the small intestine were separated 3 days after organoid transplantation and the liver was separated after 7 days to determine whether the organoids were attached. As a result, it was found that the organoids were successfully attached to the liver and integrated with the existing liver tissue (FIG. 13A and FIG. 13B).

Figure 13C:
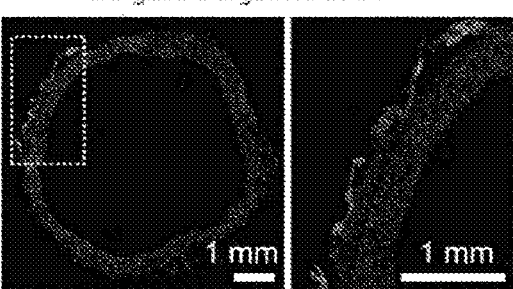
FIG. 13C shows the result of checking whether organoids are engrafted after fluorescent dye-labeled organoids are transplanted into the stomach by using the HA-CA hydrogel patch.
Figure 13D:
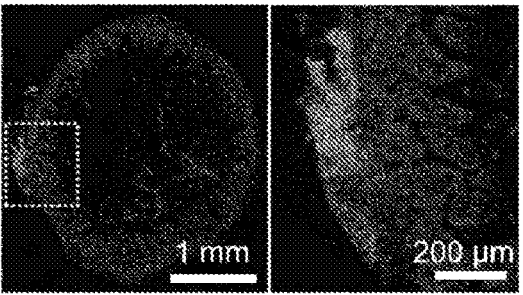
FIG. 13D shows the result of checking whether organoids are engrafted after fluorescent dye-labeled organoids are transplanted into the small intestine by using the HA-CA hydrogel patch.

Also, it was found that the organoids were successfully attached to the stomach and the small intestine (FIG. 13C and FIG. 13D).

(2) Formation of Multi-Layered Structure in the Form of Sheet

Since in vivo tissues such as skin and blood vessels have a multi-layered structure, the HA-CA hydrogel patch of the present disclosure was fabricated to have a multi-layered structure similar to that of the in vivo tissue.

Red and green HA-CA hydrogel patches were fabricated using color inks, and a multi-layered patch structure was formed by placing one HA-CA hydrogel patch on the other HA-CA hydrogel patch. Here, the adhesiveness of the HA-CA hydrogel patch itself was used without using a separate adhesive. As a result of test, patch structures having three layers and five layers, respectively, were fabricated (FIG. 14A).

Further, a multi-layered three-dimensional cell structure was formed by repeatedly placing hADSCs labeled with a fluorescent material on one HA-CA hydrogel patch, placing another HA-CA hydrogel patch thereon and placing hAD-SCs labeled with a fluorescent material thereon again. Here, hADSCs labeled with a different fluorescent material were used for each layer. As a result, it was confirmed that a tissue structure in the form of a multi-layered sheet in which different cells exist for each layer can be implemented using the HA-CA hydrogel patch (FIG. 14B).

Figure 15C:
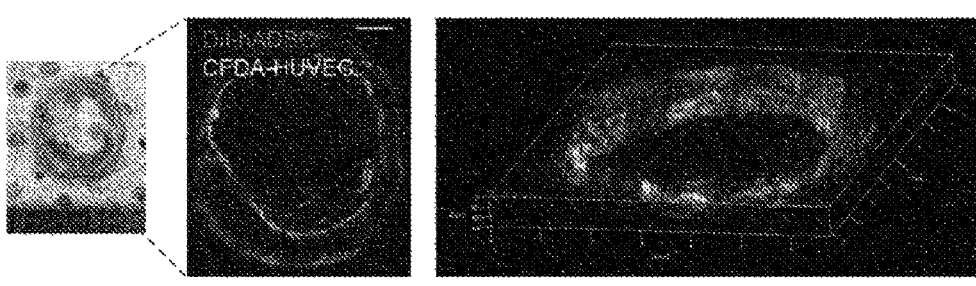
FIG. 15C shows the result of fabrication of a multi-layered HA-CA hydrogel patch in the form of a tube (A and B) and the result of fabrication of a multi-layered blood vessel-inspired structure using the same (C).

After the red and green HA-CA hydrogel patches were wound around a cylindrical mold, the mold was removed to make a tube-shaped multi-layered HA-CA hydrogel patch (FIG. 15A). It was confirmed that since the HA-CA hydrogel patch has elasticity, even when the HA-CA hydrogel patch was deformed by the pressure, it was restored back to its original shape (FIG. 15B). When the tube-shaped multi-layered HA-CA hydrogel patch was fabricated, human vascular endothelial cells (HUVECs) were attached to one layer and hADSCs were attached to the other layer. As a result, a structure similar to that of human blood vessels could be fabricated.

Example 1-5: Drug Delivery Using HA-CA Hydrogel Patch (1) Check on Drug Release Pattern An HA-CA hydrogel patch was fabricated according to the method of Preparation Example 1, and a vascular endothelial growth factor (hereinafter, referred to as "VEGF") was sprayed on the patch and then, an oxidant was applied to encapsulate VEGF in the patch (Patch (CA)-VEGF Test Group). As a comparative group, an HA-CA hydrogel patch was fabricated by mixing an HA-CA aqueous solution and VEGF and freeze-drying the mixture and then an oxidant was applied thereto (Patch (CA)-VEGF/FD Test Group). The comparison group is a drug delivery form that is considered to be the most convenient when the HA-CA hydrogel patch is used in actual clinical practice. The two types of HA-CA hydrogel patches containing VEGF were immersed in PBS at 37° C., and the VEGF release pattern depending on the presence or absence of hyaluronidase treatment was analyzed through ELISA.

Figure 16:
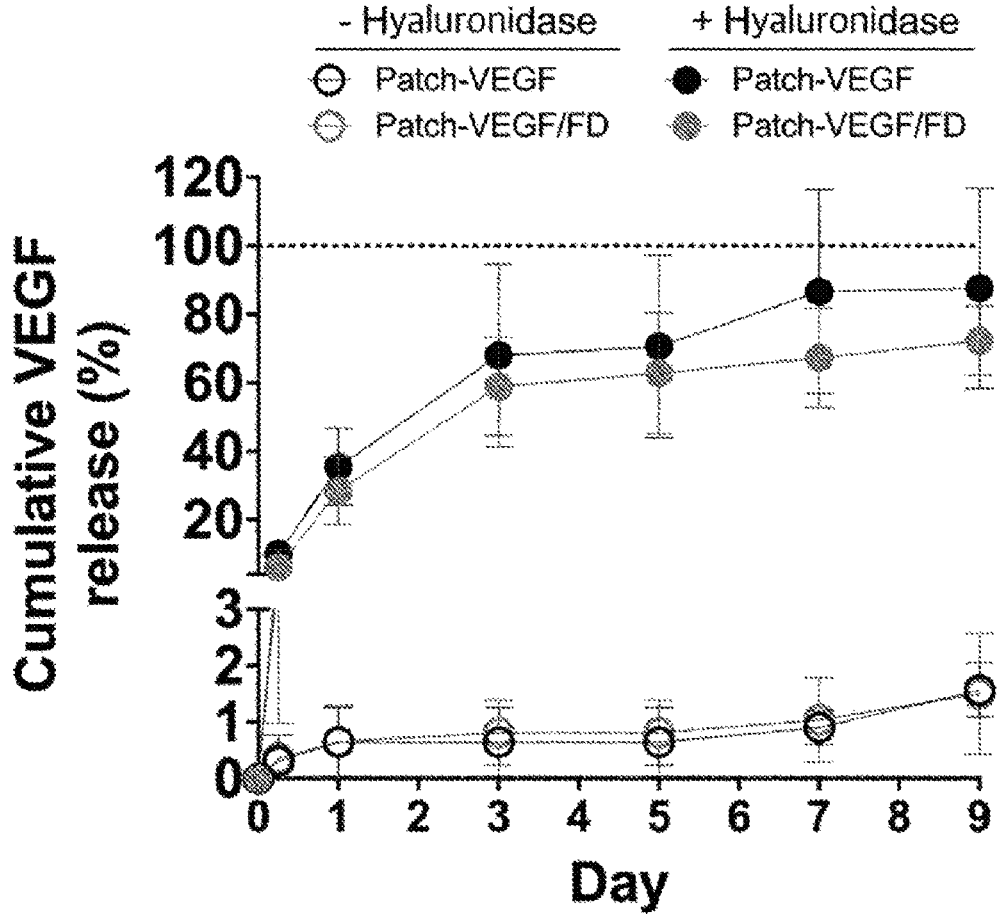
FIG. 16 shows the result of checking the drug release pattern of the HA-CA hydrogel patch under conditions mimicking an in vivo environment in the presence of hyaluronidase.

As a result of analysis, it was found that both the HA-CA hydrogel patch in which VEGF was freeze-dried together and the HA-CA hydrogel patch in which VEGF was separately introduced showed similar VEGF release patterns (FIG. 16). Further, it was found that due to strong bonds between various nucleophilic functional groups of protein and catechol, VEGF was not released well in an environment without a degrading enzyme (-hyaluronidase), whereas VEGF was released effectively in an environment treated with a degrading enzyme that mimics an in vivo environment (+hyaluronidase) (FIG. 16).

Therefore, it is expected that the use of the HA-CA hydrogel patch of the present disclosure can effectively deliver a drug to a wound site where the activity of hyaluronidase increased and enhance the healing effects of the wound site.

(2) Evaluation of Mouse Wound Healing Efficacy

Figure 17A:
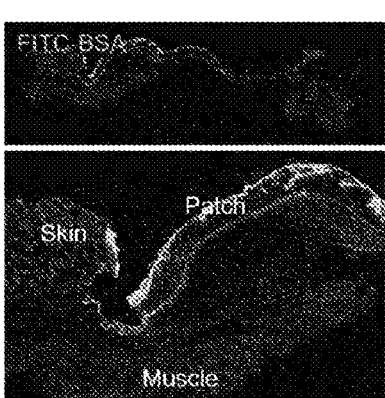
FIG. 17A shows the result of checking the wound healing effect over time after a vascular endothelial growth factor (VEGF) is introduced into a mouse wound model by using the HA-CA hydrogel patch.

After a wound with a diameter of 8 mm was made on the back of a mouse using a punch, the HA-CA hydrogel patch was put on the wound and FITC-BSA protein was sprayed on the patch. Then, an oxidant was applied to crosslink the patch. After a predetermined period of time, the tissue of the wound site was separated and stained. As a result, it was confirmed that the HA-CA hydrogel patch loaded with FITC-BSA protein was firmly attached to the muscle layer of the wound site (FIG. 17A).

A wound with a diameter of 8 mm was made on the back of mice using a punch and then, the mice were divided into 4 groups to check the skin regeneration and wound healing effect of the HA-CA hydrogel patch: 1. Control Group (No treatment); 2. Only HA-CA hydrogel patch (Patch(CA) only); 3. VEGF encapsulation in HA-CA hydrogel patch (Patch(CA)-VEGF); and 4. Patch fabricated by mixing and freeze-drying VEGF and HA-CA solution, followed by crosslinking (Freeze-dried patch; Patch(CA)-VEGF/FD).

Figure 17B:
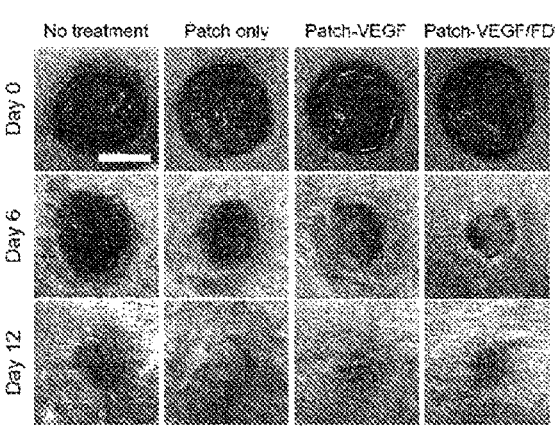
FIG. 17B shows the result of checking the wound healing effect over time after a vascular endothelial growth factor (VEGF) is introduced into a mouse wound model by using the HA-CA hydrogel patch.
Figure 17C:
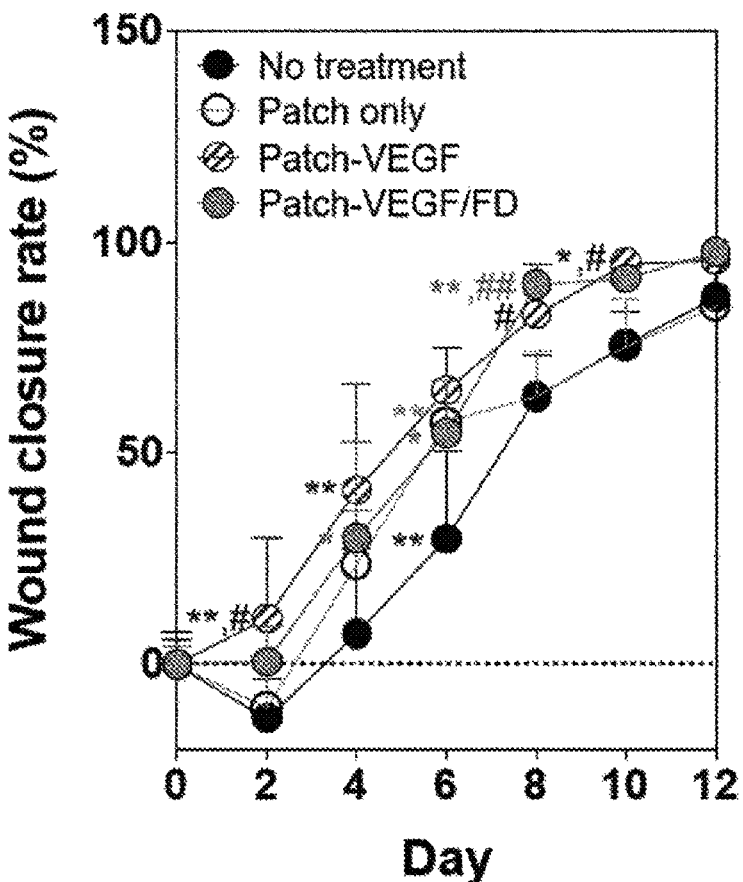
FIG. 17C shows the result of checking the wound healing effect over time after a vascular endothelial growth factor (VEGF) is introduced into a mouse wound model by using the HA-CA hydrogel patch.

As a result, it was found that the wound size was significantly decreased in Patch(CA)-VEGF Group and Patch(CA)-VEGF/FD Group in which VEGF was delivered to the wound site, and these two groups showed similar wound healing efficacy (FIG. 17B and FIG. 17C). This result shows that even when the HA-CA hydrogel patch on which a drug was already loaded was freeze-dried, there was no significant difference in the effect of the drug. Thus, it is possible to increase the user's convenience.

To evaluate the level of skin regeneration at the wound site, on the 12th day of test, the wound site was stained with hematoxylin and eosin and examined through image-based quantitative analysis.

As a result, it was found that hair follicle regeneration actively occurred in Patch(CA)-VEGF Group and Patch(CA)-VEGF/FD Group in which VEGF was delivered to the wound site (FIG. 18A and FIG. 18C). Also, it was confirmed from Masson's trichrome staining that collagen regeneration was also increased in Patch(CA)-VEGF Group and Patch(CA)-VEGF/FD Group in which VEGF was delivered to the wound site (FIG. 18B and FIG. 18D). As a result of immunostaining with a capillary marker (CD31) to check the angiogenesis effect, it was found that more blood vessels were formed in Patch(CA)-VEGF Group and Patch(CA)-VEGF/FD Group in which VEGF was delivered to the wound site (FIG. 18E and FIG. 18F).

(3) Comparison of Mouse Wound Healing Efficacy

A wound with a diameter of 8 mm was made on the back of a mouse using a punch, and the HA-CA hydrogel patch and the HA-CA bulk hydrogel were compared in terms of wound healing effect. Specifically, VEGF was mixed in advance with an HA-CA solution and the mixture was freeze-dried and then dissolved in PBS, followed by cross-linking in the form of HA-CA bulk hydrogel (Freeze-dried bulk hydrogel; Bulk(CA)-VEGF/FD). An HA-CA hydrogel patch was fabricated by mixing an HA-CA solution with VEGF in advance, freeze-drying the mixture in the form of a patch, and then crosslinking the patch with an oxidant (Freeze-dried patch; Patch(CA)-VEGF/FD).

As a result of observing the degree of reduction in wound size for 16 days, it was confirmed that the wound size was more rapidly decreased in Test Group (Patch(CA)-VEGF/FD) in which VEGF was delivered using the HA-CA hydrogel patch than in Test Group (Bulk(CA)-VEGF/FD) in which VEGF was delivered using the HA-CA bulk hydrogel (FIG. 19A and FIG. 19B).

Figure 20A:
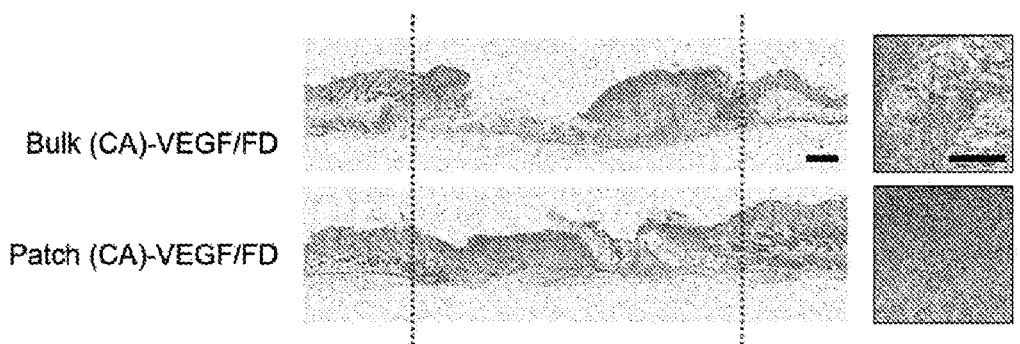
FIG. 20A shows the result of checking the degree of regeneration of a wound site through hematoxylin and eosin staining after a drug is introduced into a mouse wound model by using the HA-CA hydrogel patch or the HA-CA bulk hydrogel.
Figure 20B:
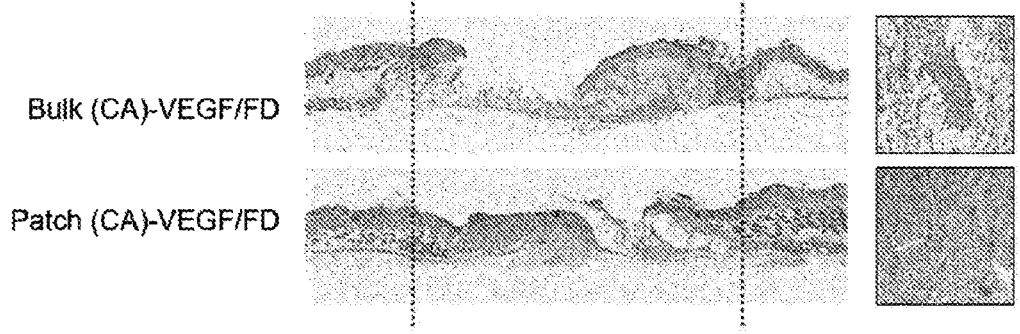
FIG. 20B shows the result of checking the degree of regeneration of a wound site through Masson's trichrome staining after a drug is introduced into a mouse wound model by using the HA-CA hydrogel patch or the HA-CA bulk hydrogel.

To evaluate the level of skin regeneration at the wound site, the mouse was sacrificed on the 16th day of test and the wound site was stained with hematoxylin and eosin. As a result, it was confirmed that more cells were generated and the wound site was more remarkably regenerated in Test Group (Patch(CA)-VEGF/FD) in which VEGF was delivered using the HA-CA hydrogel patch than in Test Group (Bulk(CA)-VEGF/FD) in which VEGF was delivered using the HA-CA bulk hydrogel (FIG. 20A). Also, as a result of staining the wound site with Masson's Trichrome, it was found that collagen regeneration occurred more in the Patch (CA)-VEGF/FD Test Group (FIG. 20B). The test result means that the hydrogel patch has better healing efficacy than the conventional solution-based bulk hydrogel even if they are made of the same material.

Preparation Example 2

(1) Fabrication of HA-PG Hydrogel Patch

A pyrogallol-functionalized hyaluronic acid (hereinafter, referred to as HA-PG) was dissolved in distilled water at a concentration of 1%, and 40 μl, 80 μl or 160 μl of the 1% HA-PG solution was poured into an 8 mm cylindrical mold and then freeze-dried overnight at −80° C. to prepare HA-PG hydrogel patches with thicknesses of 0.8 mm, 1.6 mm, and 3.2 mm, respectively. The prepared HA-PG hydrogel patches are in a dry state and thus are easy to store. Also, they are fabricated in the form of a thin film and thus can be easily cut into a desired shape. Therefore, they are convenient to use.

In a previous test, when the concentration of HA-PG is higher than 1%, the hydrogel patch is so hard that cells and a drug cannot effectively penetrate into the hydrogel patch, and when the concentration of HA-PG is low, the structure of the hydrogel patch is not sufficiently maintained and the cells and drug are lost. Also, when the HA-PG hydrogel patch is too thick, the cells and drug cannot effectively penetrate into the hydrogel patch, and when the HA-PG hydrogel patch is too thin, it is difficult to handle the hydrogel patch and the structure of the hydrogel patch cannot be maintained for a long time after an oxidant is applied. In Examples 2-1 to 2-3, an HA-PG hydrogel patch with a thickness of 1.6 mm was used.

(2) Fabrication of HA-PG Bulk Hydrogel

HA-PG was dissolved in phosphate-buffered saline (PBS), and a sodium periodate solution was added into the solution (HA-PG solution:oxidant solution=3:1 (v/v)) to prepare an HA-PG bulk hydrogel. A final concentration of HA-PG in the prepared HA-PG bulk hydrogel was 1%. The prepared HA-PG bulk hydrogel was used for analyzing the structure.

In a cell transplantation and drug delivery test, an HA-PG bulk hydrogel not treated with a sodium periodate solution was used to allow natural oxidation to occur in the body.

Figure 21A:
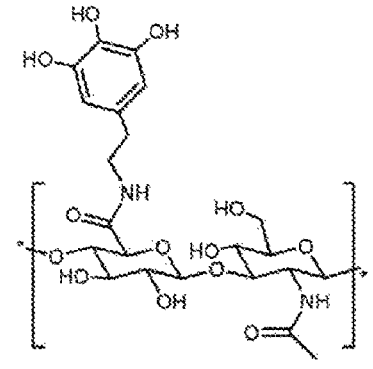
FIG. 21A shows the molecular structure of a pyrogallol-functionalized hyaluronic acid (HA-PG).
Figure 21B:
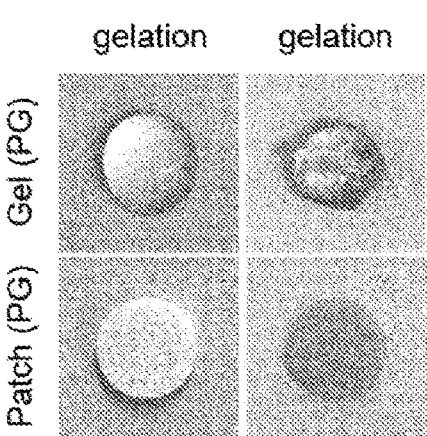
FIG. 21B shows an HA-PG hydrogel patch and an HA-PG bulk hydrogel in a gelated form.
Figure 21C:
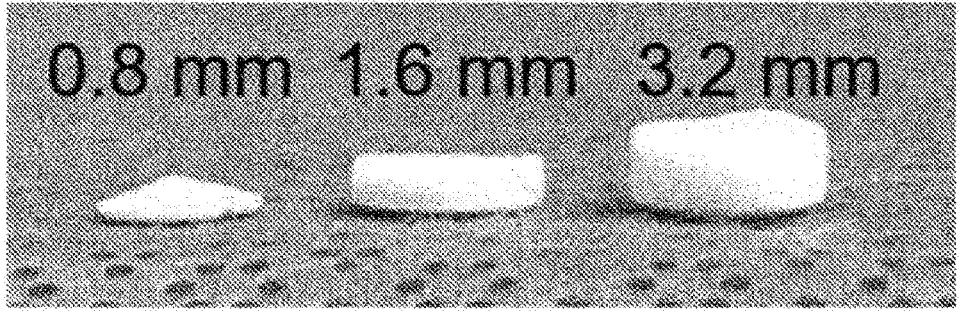
FIG. 21C shows HA-PG hydrogel patches with different thicknesses.
Figure 27A:
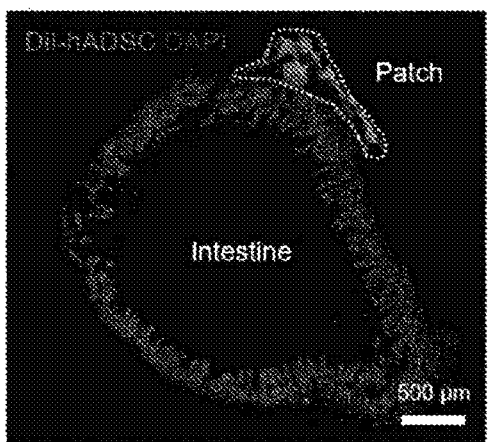
FIG. 27A shows the result of checking whether stem cells are engrafted after the stem cells are transplanted into the small intestine by using the HA-PG hydrogel patch.
Figure 27B:
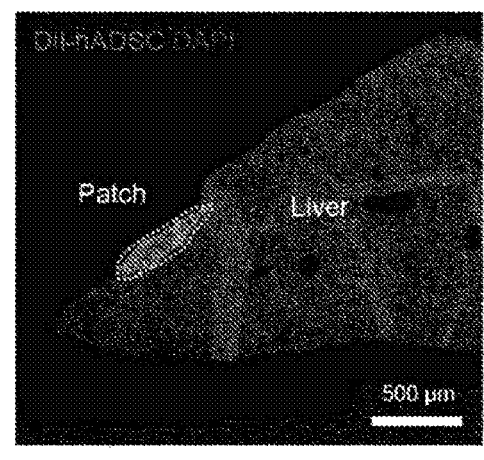
FIG. 27B shows the result of checking whether stem cells are engrafted after the stem cells are transplanted into the liver by using the HA-PG hydrogel patch.
Figure 27C:
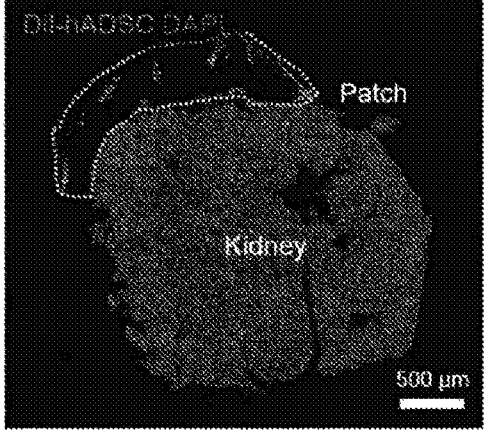
FIG. 27C shows the result of checking whether stem cells are engrafted after the stem cells are transplanted into the kidney by using the HA-PG hydrogel patch.
Figure 27D:
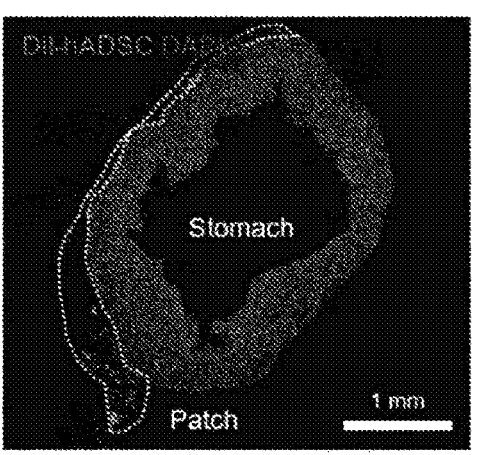
FIG. 27D shows the result of checking whether stem cells are engrafted after the stem cells are transplanted into the stomach by using the HA-PG hydrogel patch.

FIG. 21A shows the molecular structure of HA-PG, FIG. 21B shows an HA-PG hydrogel patch and an HA-PG bulk hydrogel in a gelated form, and FIG. 21C shows HA-PG hydrogel patches with different thicknesses.

Example 2-1: Characterization of HA-PG Hydrogel Patch (1) Check on Cytotoxicity The HA-PG hydrogel patch or the HA-PG bulk hydrogel prepared in Preparation Example was placed on the bottom of a 6-well cell culture plate, and human adipose-derived stem cells (hADSCs) were dispensed and cultured for 7 days. The cell viability was checked using Live/Dead assay (Invitrogen; USA) according to the manufacturer's protocol on days 0, 3 and 7 of culture.

As a result, it was found that both the HA-PG bulk hydrogel (Gel(PG)) and the HA-PG hydrogel patch (Patch (PG)) had no cytotoxicity (FIG. 22). This result means that even when the form of the HA-PG bulk hydrogel was modified into an HA-PG hydrogel patch, the biocompatibility of hyaluronic acid was maintained.

(2) Check on Swelling Ratio and Degradation Ratio

An HA-PG hydrogel patch or an HA-PG bulk hydrogel was immersed in PBS at 37° C. similar to in vivo conditions for 7 days, and the swelling ratio was measured after 9 hours, 1 day, 3 days and 7 days. As a result of measurement, the swelling ratio of the HA-PG hydrogel patch was about 2 times higher than that of the HA-PG bulk hydrogel (FIG. 23A and FIG. 23B). This result means that the HA-PG hydrogel patch has a denser internal structure than the HA-PG bulk hydrogel.

Since various degrading enzymes exist in the actual in vivo environment, the HA-PG hydrogel patch or the HA-PG bulk hydrogel was immersed in PBS at 37° C. and then treated with a hyaluronidase until degradation. The weights of the HA-PG hydrogel patch and the HA-PG bulk hydrogel were measured at regular time intervals to measure the degrees of degradation over time. As a result of measurement, the HA-PG bulk hydrogel was rapidly degraded after treatment with a hyaluronidase and completely degraded within 24 hours. The HA-PG hydrogel patch remained even after 600 hours from the treatment with a hyaluronidase. Thus, it was found that the rate of degradation of HA-PG hydrogel patch is slower than that of HA-PG bulk hydrogel (FIG. 23C).

(3) Check on Internal Structure

The internal structures of the HA-PG hydrogel patch (Patch(PG)) and the HA-PG bulk hydrogel (Gel(PG)) were examined under a scanning electron microscope. As a result, it was confirmed that the HA-PG bulk hydrogel had a porous structure of micrometer (μm) size, whereas the HA-PG hydrogel patch had a denser nanofiber-based porous structure (FIG. 24).

This result means that the HA-PG hydrogel patch can have a denser internal structure than the HA-PG bulk hydrogel and the surface area functionalized with pyrogallol is greatly increased, and, thus, the mechanical properties and adhesion ability become excellent.

(4) Measurement of Mechanical Strength

The elastic moduli of the HA-PG hydrogel patch (Patch (PG)) and the HA-PG bulk hydrogel (Gel(PG)) were measured at a frequency of from 0.1 Hz and 10 Hz by using a rheometer.

As a result of measurement, both the HA-PG hydrogel patch and the HA-PG bulk hydrogel showed higher G' values than G" values. Thus, it was found that the internal structure is formed of a stable polymer network (FIG. 25A). Further, the average elastic modulus of the HA-PG bulk hydrogel was about 1.5 kPa, whereas the elastic modulus of the HA-PG hydrogel patch was about 18 kPa. Thus, it was found that the elastic modulus increased by about 10 times or more (FIG. 25B). As a result of measuring the elastic moduli of the HA-PG hydrogel patches with different thicknesses prepared in Preparation Example 1, it was found that the elastic modulus significantly increased from 5 kPa to 27 and 46 kPa as the thickness of the patch increased (FIG. 25C). The increase in the elastic modulus means that the mechanical strength becomes excellent.

The above test results mean that the HA-PG hydrogel patch has a remarkably higher mechanical strength than the HA-PG bulk hydrogel and the mechanical strength of the HA-PG hydrogel patch can be easily regulated by regulating the thickness of the HA-PG hydrogel patch.

(5) Measurement of Tissue Adhesion

After the skin on the back of a mouse was incised, the HA-PG hydrogel patch (Patch(PG)) or the HA-PG bulk hydrogel (Gel(PG)) was placed thereon and then, crosslinking (attachment) of the patch was induced by means of natural oxidation using dissolved oxygen in the body. After the crosslinking by means of natural oxidation was completed (within about 5 minutes), the skin tissue was removed. Then, the amount of force to remove the HA-PG bulk hydrogel or HA-PG hydrogel patch from the skin tissue was measured by the tack test method to compare the tissue adhesion.

As a result of measurement, it was found that the HA-PG bulk hydrogel had an adhesion of about 1.6 N, whereas the HA-PG hydrogel patch had an adhesion of about 4 N, indicating that the tissue adhesion was improved by 2.5 times or more (FIG. 26A and FIG. 26B).

Further, the area of the adhesion-extension length graph (FIG. 26A) was measured to calculate the amount of work (work of adhesion) required to separate the HA-PG bulk hydrogel or hydrogel patch attached to the skin. As a result, it was found that the work of adhesion of the HA-PG hydrogel patch increased by 2.5 times or more compared with the HA-PG bulk hydrogel (FIG. 26C).

Example 2-2: HA-PG Hydrogel Patch Efficacy in Cell Transplantation (1) Stem Cell Transplantation After a mouse was anesthetized, the HA-PG hydrogel patch was placed on the small intestine, liver and kidney by abdominal incision. Then, hADSCs labeled with Dil fluorescence were dropped, followed by suturing. After 24 hours, the mouse was sacrificed to separate the kidney, liver and intestine. After a visual check on whether the HA-PG hydrogel patch was attached, whether hADSCs were engrafted was observed. As a result, it was found that the HA-PG hydrogel patch was attached well to the surface of the organ with high water content even after 24 hours. Also, the tissue staining result shows that the HA-PG hydrogel patch was attached to the small intestine, liver and kidney and hADSCs were also attached (FIG. 27).

This result means that the HA-PG hydrogel patch can be attached to various organs and tissues in an in vivo environment with high water content so that non-invasive cell transplantation into various organs and tissues is possible.

(2) Transplantation of Organoid

Although organoids have excellent healing efficacy such as tissue regeneration, no effective transplantation methods have been developed due to their large size. Therefore, it was checked whether the HA-PG hydrogel patch of the present disclosure can be used for organoid transplantation.

Figure 28A:
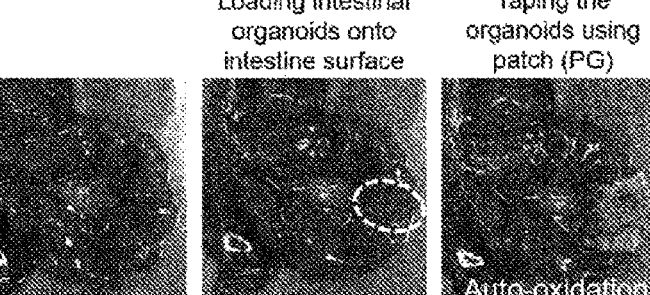
FIG. 28A shows a schematic process of transplanting fluorescent material-labeled organoids into the small intestine by using the HA-PG hydrogel patch.
Figure 28B:
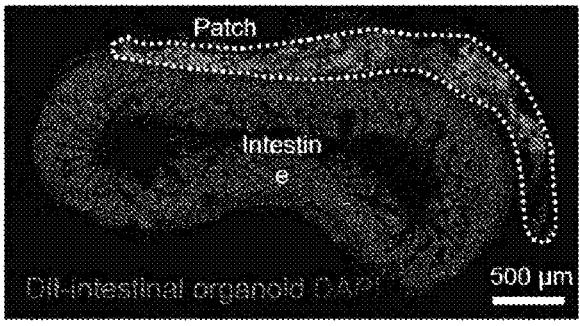
FIG. 28B shows the result of checking whether organoids are attached to the small intestine.
Figure 28C:
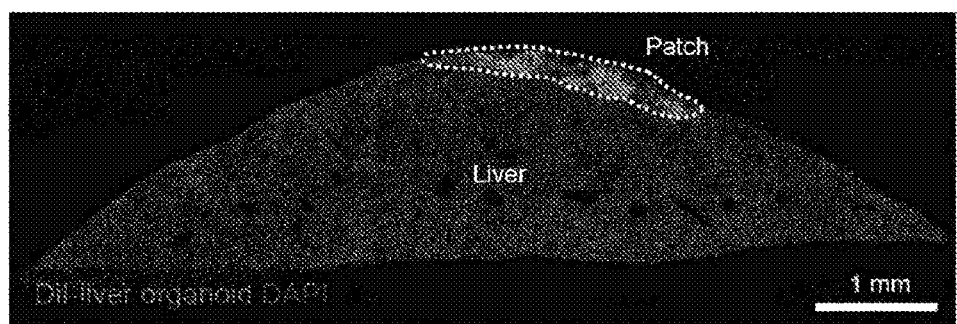
FIG. 28C shows the result of checking whether organoids are attached to the liver.
Figure 28D:
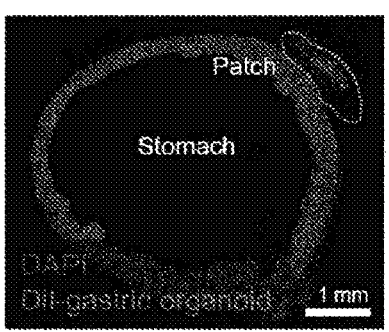
FIG. 28D shows the result of checking whether organoids are attached to the stomach.

Organoids labeled with Dil fluorescence were placed on the small intestine, liver or stomach, and the HA-PG hydrogel patch was attached to fix the organoids on the surface of each organ by means of natural oxidation (FIG. 28A). After 24 hours, the tissue in the site where the organoids were transplanted was separated and stained. As a result, it was found that the transplanted organoids were successfully attached to each organ and integrated with the existing organ (the small intestine in FIG. 28B, the liver FIG. 28C and the stomach tissue in FIG. 28D).

As a result of the test described above, it can be seen that the HA-PG hydrogel patch is crosslinked by means of natural oxidation using dissolved oxygen in the body, and, thus, large organoids can be firmly fixed to a target site and transplanted into the target site by a one-step method by which the HA-PG hydrogel patch and organoids are attached to the target site.

(3) Wound Healing Efficacy

Diabetes is a metabolic disease caused by a lack of insulin secretion or insulin resistance and can lead to various complications such as diabetic retinopathy and renal failure. In particular, it causes diabetic wounds such as diabetic foot ulcers. Diabetic wounds are much more difficult to heal and regenerate than ordinary wounds due to blood circulation disorders and high blood sugar levels. Therefore, it was checked whether the HA-PG hydrogel patch of the present disclosure can be used for healing diabetic wounds.

A mouse was fasted for 24 hours, and streptozotocin, which is a drug that selectively damages pancreatic $\beta$-cells, was administered intraperitoneally at a concentration of 100 mg/kg to induce diabetes. After 2 weeks, a change in blood sugar was measured, and it was determined that diabetes was induced when the blood sugar was 300 mg/dL or more.

A wound with a diameter of 8 mm was made on the back of diabetes-induced mice using a punch and then, the mice were divided into 6 groups and dispensed with hADSCs to check the skin regeneration and wound healing effect: 1. Control Group (No treatment); 2. Only HA-PG bulk hydrogel (Gel(PG) only); 3. Only HA-PG hydrogel patch (Patch (PG) only); 4. Only hADSCs applied directly (hADSC only); 5. Mixture of HA-PG bulk hydrogel and hADSCs (Gel(PG)-hADSC); and 6. HA-PG hydrogel patch placed on wound site and hADSCs dispensed thereon (Patch(PG)-hADSC).

Figure 29:
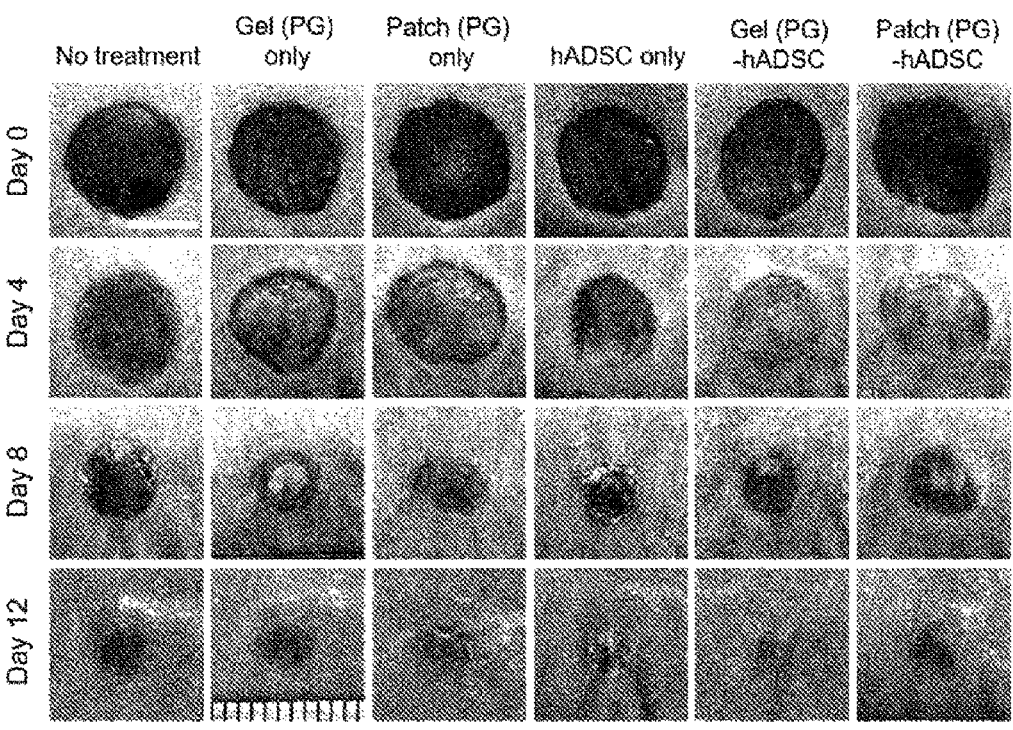
FIG. 29 shows the result of checking changes in size of a wound over time after the HA-PG hydrogel patch and human adipose-derived stem cells (hADSCs) are applied to a diabetic mouse wound model.

As a result of observing a change in size of the wound for 12 days, it was found that the wound size was most rapidly decreased in Patch(PG)-hADSC in which the HA-PG hydrogel patch was placed on the wound site and hADSCs were dispensed thereon (FIG. 29).

Figure 30A:
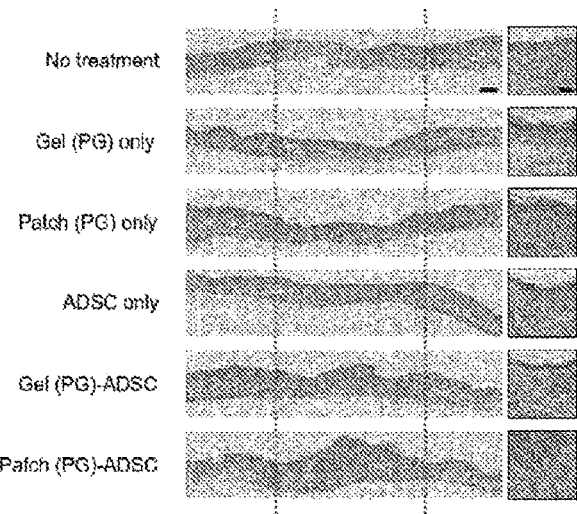
FIG. 30A shows the result of checking the hair follicle regeneration at a wound site after the HA-PG hydrogel patch and hADSCs are applied to a diabetic mouse wound model.
Figure 30B:
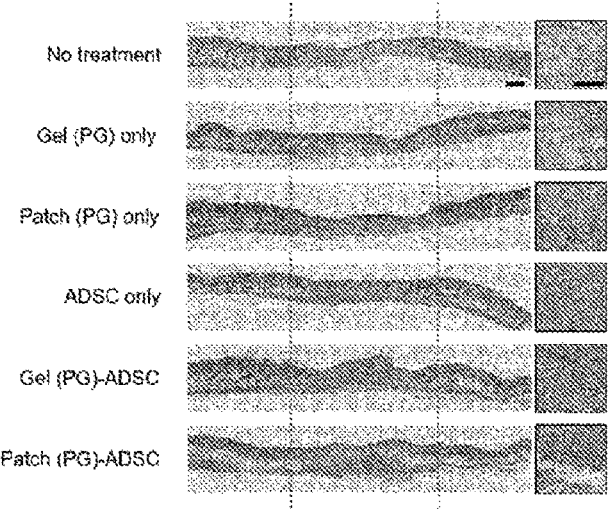
FIG. 30B shows the result of checking the collagen production at a wound site after the HA-PG hydrogel patch and hADSCs are applied to a diabetic mouse wound model.
Figure 30C:
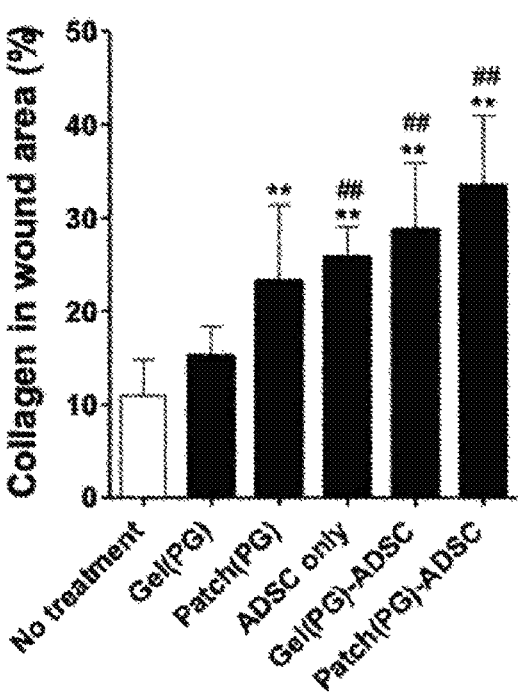
FIG. 30C shows the result of checking the collagen production at a wound site after the HA-PG hydrogel patch and hADSCs are applied to a diabetic mouse wound model.

On the 12th day of the test, the tissue was separated from the wound site to check the level of skin regeneration. As a result of staining the tissue with hematoxylin and eosin, it was found that hair follicles were regenerated in Patch(PG)-hADSC Group in which the HA-PG hydrogel patch was placed on the wound site and hADSCs were dispensed thereon. Thus, it was confirmed that mature tissue regeneration occurred in Patch(PG)-hADSC Group compared with the other groups (FIG. 30A). Also, it was confirmed from Masson's trichrome staining that collagen regeneration also occurred most actively in Patch(PG)-hADSC Group (FIG. 30B and FIG. 30C).

It can be seen from the above-described result of test that if the HA-PG hydrogel patch is placed on the wound site, it is crosslinked by means of natural oxidation in an environment containing oxygen in the body, such as body fluids, without treatment with an oxidant, and, thus, cell transplantation can be performed easily. Also, it is possible to avoid side effects of the oxidant. Therefore, the HA-PG patch is considered to be a suitable formulation for clinical application. Further, it can be seen that the HA-PG hydrogel patch of the present disclosure can be usefully used for healing diabetic wounds which are more difficult to heal and recover than ordinary wounds and in which tissue damage is gradually severe.

Example 2-3: Drug Delivery Using HA-PG Hydrogel Patch

Mouse models of diabetes were prepared in the same manner as in Example 2-3. A wound with a diameter of 8 mm was made on the back of the diabetes-induced mice using a punch and then, the mice were divided into 6 groups and applied with a platelet-derived growth factor (PDGF) to check the skin regeneration and wound healing effect: Control Group (No treatment); Only HA-PG bulk hydrogel (Gel(PG) only); Only HA-PG hydrogel patch (Patch (PG) only); PDGF encapsulation in HA-PG bulk hydrogel (Gel (PG)-PDGF); PDGF encapsulation in HA-PG hydrogel patch (Patch (PG)-PDGF); and Patch fabricated by mixing and freeze-drying PDGF and HA-PG solution, followed by crosslinking (Freeze-dried patch; Patch (PG)-PDGF/FD).

Figure 31A:
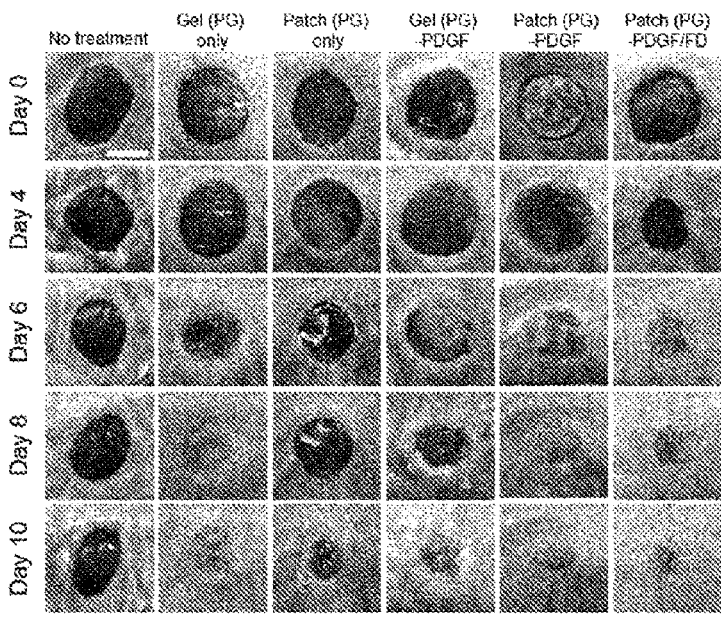
FIG. 31A shows the result of checking the wound healing effect over time after the HA-PG hydrogel patch and a platelet-derived growth factor (PDGF) are applied to a diabetic mouse wound model.
Figure 31B:
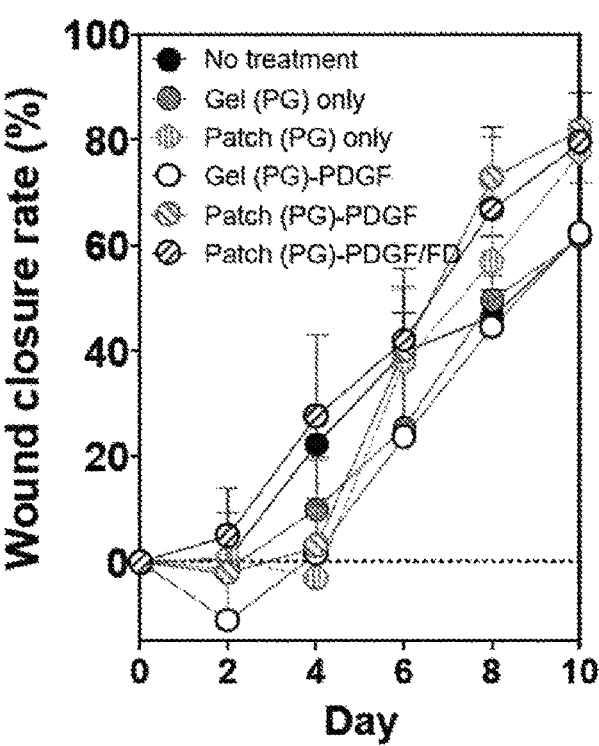
FIG. 31B shows the result of checking the wound healing effect over time after the HA-PG hydrogel patch and a platelet-derived growth factor (PDGF) are applied to a diabetic mouse wound model.

As a result of observing a decrease in size of the wound for 10 days, it was found that about 80% of the wound recovered on day 10 in Patch(PG)-PDGF Group and Patch (PG)-PDGF/FD Group in which the HA-PG hydrogel patch was applied, whereas about 60% of the wound recovered in Group in which the HA-PG bulk hydrogel was applied and Control Group (FIG. 31A and FIG. 31B). Also, there was no significant difference in wound healing efficacy between Patch(PG)-PDGF Group and Patch(PG)-PDGF/FD Group. This result shows that even when the HA-PG hydrogel patch on which a drug was already loaded was freeze-dried, there was no significant difference in the effect of the drug.

Example 2-4: Formation of Multi-Layered Structure Using HA-PG Hydrogel Patch Since in vivo tissues such as skin and blood vessels have a multi-layered structure, the HA-PG hydrogel patch of the present disclosure was fabricated to have a multi-layered structure similar to that of the in vivo tissue.

Figure 32:
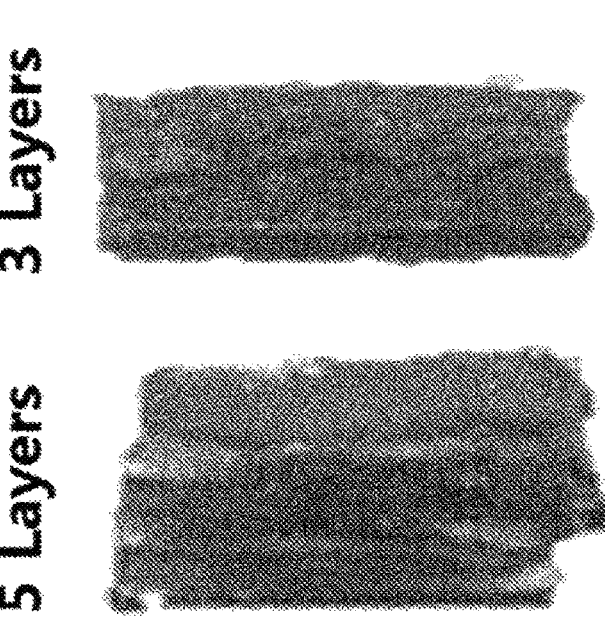
FIG. 32 shows the result of fabrication of a multi-layered structure similar to an in vivo tissue with an HA-PG hydrogel patch.

Red and green HA-PG hydrogel patches were fabricated using color inks, and a multi-layered patch structure was formed by placing one HA-PG hydrogel patch on the other HA-PG hydrogel patch. Here, the adhesiveness of the HA-PG hydrogel patch itself was used without using a separate adhesive. As a result of test, patch structures having three layers and five layers, respectively, were fabricated (FIG. 32).

We claim:

1. A drug or cell delivery system comprising a biocompatible polymer functionalized with a catechol group, wherein the drug or cell delivery system is manufactured by:
    (a) preparing a hydrogel patch by freeze-drying a solution of the biocompatible polymer functionalized with the catechol group;

(b) contacting the hydrogel patch prepared in the (a) with a drug or cells; and
    (c) contacting an oxidizing agent after the (b),
        wherein the biocompatible polymer is hyaluronic acid, and
        wherein the hydrogel patch is a thin film and can be cut into a desired shape for use as the drug or cell delivery system.

2. The drug or cell delivery system of claim 1, wherein the catechol group is derived from a catechol-based compound selected from the group consisting of catechol, 4-tert-butyl-catechol (TBC), urushiol, alizarin, dopamine, dopamine hydrochloride, 3,4-dihydroxyphenylalanine (DOPA), caffeic acid, norepinephrine, epinephrine, 3,4-dihydroxyphenylacetic acid (DOPAC), isoprenaline, isoproterenol, and 3,4-dihydroxybenzoic acid.

3. The drug or cell delivery system of claim 1, wherein the hydrogel patch has a thickness of from 0.05 mm to 10.0 mm.

4. The drug or cell delivery system of claim 1, wherein the drug is selected from the group consisting of a vascular endothelial growth factor (VEGF), an epidermal growth factor (EGF), a keratinocyte growth factor (KGF), a growth and differentiation factor, a hepatocyte growth factor (HGF), a platelet-derived growth factor (PDGF), a transforming growth factor (TGF), angiopoietin, erythropoietin, a bone morphogenetic protein (BMP), an insulin-like growth factor, an acidic and basic fibroblast growth factor, a granulocyte-macrophage colony-stimulating factor (GM-CSF), a brain-derived neurotrophic factor, a glial cell-derived neurotrophic factor, a nerve growth factor, a stromal cell-derived factor-1 (SDF-1), a substance P (SP), a hypoxia-inducible factor-1 (HIF-1), a Dickkopf-related protein-1 (DKK-1), an interleukin, pembrolizumab, nivolumab, atezolizumab, ipilimumab, blinatumomab, trastuzumab, cetuximab, and bevacizumab.

5. The drug or cell delivery system of claim 1, wherein the drug is selected from the group consisting of acemethacin, acrivastine, aldosterone, antazoline, astemizole, azatadine, azelastine, beclomethasone, betamethasone, bromfenac, buclizine, carprofen, cetirizine, chlorophyllin, chlorpheniramine, clemastine, cromolyn, cyclizine, cyproheptadine, dexamethasone, diazolinum, diclofenac, diphenhydramine, ebastine, emedastine, epinastine, etodolac, fenbufen, fenoprofen, fexofenadine, fludrocortisone, flurbiprofen, fluorometholone, hydroxyzine, ibuprofen, indomethacin, ketoprofen, ketorolac tromethamine, ketotifen, levocabastine, levocetirizine, lodoxamide, loratadine, loteprednol, loxoprofen, medrysone, mepivacaine, mequitazine, methdilazine, methapyrilene, nabumetone, naphazoline, naproxen, nedocromil, norastemizole, norvastin, olopatadine, fenidamin, phenylephrine, oxatomide, oxymetazoline, pemirolast, pheniramine, picumast, prednisolone, promethazine, rimexolone, repirinast, montelukast, sulindac, suprofen, zafirlukast, tetrahydrozoline, terfenadine, tiaprofenic acid, tometim, tranilast, triamcinolone, trimeprazine, triprolidine, donepezil, rivastigmine, galantamine, memantine, lidocaine, ketamine, methotrexate, cyclosporine, cisplatinum, capecitabine, oxaliplatin, doxorubicin, mitomycin-C, daunomycin, epirubicin, tamoxifen, sorafenib, 5-fluorouracil, paclitaxel, dexibuprofen, piroxicam, and pharmaceutically acceptable salts and mixtures thereof.

6. A method of manufacturing a drug or cell delivery system, comprising:
    (a) preparing a hydrogel patch by freeze-drying a solution of a biocompatible polymer functionalized with a catechol group; and (b) contacting the hydrogel patch prepared in the (a) with the drug or cells; and (c) contacting an oxidizing agent after the (b), wherein the biocompatible polymer is hyaluronic acid, and wherein the hydrogel patch is a thin film and can be cut into a desired shape for use as the drug or cell delivery system.

7. The method of manufacturing a drug or cell delivery system of claim 6, wherein the drug in the (b) is selected from the group consisting of a vascular endothelial growth factor (VEGF), an epidermal growth factor (EGF), a keratinocyte growth factor (KGF), a growth and differentiation factor, a hepatocyte growth factor (HGF), a platelet-derived growth factor (PDGF), a transforming growth factor (TGF), angiopoietin, erythropoietin, a bone morphogenetic protein (BMP), an insulin-like growth factor, an acidic and basic fibroblast growth factor, a granulocyte-macrophage colony-stimulating factor (GM-CSF), a brain-derived neurotrophic factor, a glial cell-derived neurotrophic factor, a nerve growth factor, a stromal cell-derived factor-1 (SDF-1), a substance P (SP), a hypoxia-inducible factor-1 (HIF-1), a Dickkopf-related protein-1 (DKK-1), an interleukin, pembrolizumab, nivolumab, atezolizumab, ipilimumab, blinatumomab, trastuzumab, cetuximab, and bevacizumab.

8. The method of manufacturing a drug or cell delivery system of claim 6, wherein the drug in the (b) is selected from the group consisting of acemethacin, acrivastine, aldosterone, antazoline, astemizole, azatadine, azelastine, beclomethasone, betamethasone, bromfenac, buclizine, carprofen, cetirizine, chlorophyllin, chlorpheniramine, clemastine, cromolyn, cyclizine, cyproheptadine, dexamethasone, diazolinum, diclofenac, diphenhydramine, ebastine, emedastine, epinastine, etodolac, fenbufen, fenoprofen, fexofenadine, fludrocortisone, flurbiprofen, fluorometholone, hydroxyzine, ibuprofen, indomethacin, ketoprofen, ketorolac tromethamine, ketotifen, levocabastine, levocetirizine, lodoxamide, loratadine, loteprednol, loxoprofen, medrysone, mepivacaine, mequitazine, methdilazine, methapyrilene, nabumetone, naphazoline, naproxen, nedocromil, norastemizole, norvastin, olopatadine, fenidamin, phenylephrine, oxatomide, oxymetazoline, pemirolast, pheniramine, picumast, prednisolone, promethazine, rimexolone, repirinast, montelukast, sulindac, suprofen, zafirlukast, tetrahydrozoline, terfenadine, tiaprofenic acid, tometim, tranilast, triamcinolone, trimeprazine, triprolidine, donepezil, rivastigmine, galantamine, memantine, lidocaine, ketamine, methotrexate, cyclosporine, cisplatinum, capecitabine, oxaliplatin, doxorubicin, mitomycin-C, daunomycin, epirubicin, tamoxifen, sorafenib, 5-fluorouracil, paclitaxel, dexibuprofen, piroxicam, and pharmaceutically acceptable salts and mixtures thereof.

9. The method of manufacturing a drug or cell delivery system of claim 6, wherein the cells of the (b) are selected from the group consisting of stem cells, vascular endothelial cells, osteoblasts, chondrocytes, cardiac cells, muscle cells, keratinocytes, fibroblasts, nerve cells, hepatocytes, intestinal cells, gastric cells, skin cells, adipocytes, blood cells, immune cells, cell spheroids, and organoids.

10. A method of forming a structure inspired by a biological tissue, comprising:

(a) wrapping a mold of a predetermined shape with a hydrogel patch prepared by freeze-drying a solution of a biocompatible polymer functionalized with a catechol group; and (b) contacting stem cells with the hydrogel patch; and (c) contacting an oxidizing agent after applying the cells to the hydrogel patch, wherein the biocompatible polymer is hyaluronic acid, and wherein the hydrogel patch is a thin film and can be cut into a desired shape for use in forming a structure inspired by a biological tissue.

11. The method of forming a structure inspired by a biological tissue of claim 10, wherein the stem cells of the (b) are selected from the group consigning of adult stem cells, embryonic stem cells, induced pluripotent stem cells, adipose tissue-derived stem cells, mesenchymal stem cells, placenta-derived stem cells, and neural stem cells.

* * * * *